United States Patent
Lovlekar et al.

(10) Patent No.: US 12,403,210 B2
(45) Date of Patent: Sep. 2, 2025

(54) USER EQUIPMENT HAVING MULTIPLE SUBSCRIBER IDENTITY MODULES WITH IMPROVED SUSPEND / RESUME OPERATION

(71) Applicant: Apple Inc., Cupertino, CA (US)

(72) Inventors: Srirang A. Lovlekar, Cupertino, CA (US); Sethuraman Gurumoorthy, San Jose, CA (US); Murtaza A. Shikari, Mountain View, CA (US); Srinivasan Nimmala, San Jose, CA (US); Sree Ram Kodali, San Jose, CA (US); Fangli Xu, Beijing (CN); Haijing Hu, Los Gatos, CA (US); Yuqin Chen, Beijing (CN); Dawei Zhang, Saratoga, CA (US); Longda Xing, San Jose, CA (US); Zhiwei Wang, Beijing (CN); Yaoqi Yan, Beijing (CN); Muthukumaran Dhanapal, Sunnyvale, CA (US); Beibei Wang, San Jose, CA (US); Lele Cui, Beijing (CN)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/519,287

(22) Filed: Nov. 4, 2021

(65) Prior Publication Data

US 2022/0072175 A1 Mar. 10, 2022

Related U.S. Application Data

(63) Continuation of application No. 16/915,737, filed on Jun. 29, 2020, now Pat. No. 11,197,346.

(30) Foreign Application Priority Data

Jul. 10, 2019 (CN) .......................... 201910618956.0

(51) Int. Cl.
*H04W 8/18* (2009.01)
*A61L 2/10* (2006.01)
(Continued)

(52) U.S. Cl.
CPC ......... *A61L 2/24* (2013.01); *A61L 2/10* (2013.01); *A61L 2/22* (2013.01); *G05D 1/0094* (2013.01);
(Continued)

(58) Field of Classification Search
None
See application file for complete search history.

(56) References Cited

U.S. PATENT DOCUMENTS

| | | | |
|---|---|---|---|
| 9,674,758 B2 | 6/2017 | Tsai et al. | |
| 10,568,073 B2 | 2/2020 | Pathak et al. | |

(Continued)

FOREIGN PATENT DOCUMENTS

| | | |
|---|---|---|
| CN | 106464611 | 2/2017 |
| CN | 107113586 | 8/2017 |

(Continued)

OTHER PUBLICATIONS

Intel Corporation; "Efficient RRC state transitions from RRC_Connected to RRC_Idle or to RRC_Inactive"; 3GPP TSG RAN EG2 Meeting #105bis R2-1904433; Xi'an, China; Apr. 8, 2019; 3 pages.

(Continued)

Primary Examiner — Gary Lafontant
(74) Attorney, Agent, or Firm — Kowert, Hood, Munyon, Rankin & Goetzel, P.C.

(57) ABSTRACT

Devices and associated methods for operating a dual-subscriber identity module (SIM) dual-standby (DSDS) user equipment device (UE) configured with a first SIM and a second SIM. The UE performs communications with a first cellular network using the first SIM and a first radio resource (Continued)

control (RRC) connection, and receives a request to perform a higher priority communication using the second SIM. In response to the request to perform the higher priority communication, the UE transmits a request to the first network to suspend the first RRC connection. After transmission of the request to suspend the first RRC connection, the UE receives a message from the first network to place the first RRC connection in an inactive state, and initiates a timer, wherein the timer is used to determine whether the first RRC connection remains in the inactive state or transitions to an idle state.

19 Claims, 11 Drawing Sheets

(51) Int. Cl.
*A61L 2/22* (2006.01)
*A61L 2/24* (2006.01)
*G05D 1/00* (2006.01)
*G05D 1/46* (2024.01)
*G05D 1/689* (2024.01)
*H04W 88/06* (2009.01)

(52) U.S. Cl.
CPC ............... *G05D 1/101* (2013.01); *G05D 1/46* (2024.01); *G05D 1/689* (2024.01); *A61L 2202/11* (2013.01); *A61L 2202/14* (2013.01); *A61L 2202/15* (2013.01); *A61L 2202/16* (2013.01)

(56) References Cited

U.S. PATENT DOCUMENTS

| | | |
|---|---|---|
| 2014/0220981 A1 | 8/2014 | Jheng et al. |
| 2016/0249408 A1* | 8/2016 | Thiruvenkatachari ..................... H04W 76/38 |
| 2018/0160422 A1 | 6/2018 | Pathak et al. |
| 2019/0053130 A1 | 2/2019 | Guo et al. |
| 2019/0191483 A1 | 6/2019 | Ryoo |
| 2020/0304984 A1* | 9/2020 | Dhanapal ............... H04W 76/19 |
| 2021/0282103 A1* | 9/2021 | Zhu ........................ H04W 76/15 |
| 2022/0256328 A1* | 8/2022 | Xie ........................ H04W 76/28 |

FOREIGN PATENT DOCUMENTS

| | | | |
|---|---|---|---|
| CN | 108924817 A | * | 11/2018 |
| CN | 109691219 | | 4/2019 |
| EP | 3039912 A1 | | 2/2019 |
| WO | WO-2017222344 A1 | * | 12/2017 .......... H04W 36/023 |

OTHER PUBLICATIONS

Apple; "UE Assisted RRC State Transition"; 3GPP TSG-RAN WG2 Meeting #106 R2-1907166; Reno, USA; May 13, 2019; 3 pages.
Extended European Search Report for Patent Application No. EP 20184285; Nov. 26, 2020; 11 Pages.
Office Action for CN Patent Application 201910618956.0; Jan. 17, 2024.
Office Action for CN Patent Application No. 202211120380.3; Nov. 15, 2024.
Examination Report for EP 22195444.9; Dec. 23, 2024.

* cited by examiner

USER EQUIPMENT HAVING MULTIPLE SUBSCRIBER IDENTITY MODULES WITH IMPROVED SUSPEND / RESUME OPERATION

PRIORITY CLAIMS

This application is a continuation of U.S. patent application Ser. No. 16/915,737, titled "User Equipment Having Multiple Subscriber Identity Modules with Improved Suspend/Resume Operation", filed Jun. 29, 2020, which claims benefit of priority to Chinese Application No. 201910618956.0, titled "UE Having Multiple Subscriber Identity Modules with Improved Suspend/Resume Operation", filed Jul. 10, 2019, which are both hereby incorporated by reference in their entirety as though fully and completely set forth herein.

The claims in the instant application are different than those of the parent application and/or other related applications. The Applicant therefore rescinds any disclaimer of claim scope made in the parent application and/or any predecessor application in relation to the instant application. Any such previous disclaimer and the cited references that it was made to avoid, may need to be revisited. Further, any disclaimer made in the instant application should not be read into or against the parent application and/or other related applications.

FIELD

The present disclosure relates to the field of wireless communication, and more particularly to a user equipment (UE) having multiple subscriber identity modules which performs improved network notification during SIM suspend/resume operations.

DESCRIPTION OF THE RELATED ART

Wireless communication systems are rapidly growing in usage. Further, wireless communication technology has evolved from voice-only communications to also include the transmission of data, such as Internet and multimedia content. In order to enable a wireless device to access a wireless communication network (e.g., a cellular telecommunication network) according to at least some wireless communication technologies and standards, a user may subscribe to a service provider (a "carrier"), who in turn may provide such services to the user, e.g., via a wireless communication network which they operate. Such subscribers in a wireless communication network are typically assigned subscriber identity information, which may for example be stored as part of a subscriber identity module (SIM) in the subscriber's wireless device. For example, many wireless devices may be provided with a slot for a removable subscriber identity module (SIM) card. Providing such a slot may enable users to select and/or change their subscriber identity independently from the wireless device, as the user may be able to switch out their current SIM card for a different SIM card at any given time as desired. More recently, UE devices may come equipped with an electronic SIM (eSIM), wherein an embedded memory in the UE stores subscriber identity information for the user.

Many UE devices today are being designed as dual SIM or multi SIM phones, wherein the UE is capable of storing two or more sets of subscriber identity information for the user. This enables the UE to, for example, store first subscriber identity information for a user's home telephone number and also store second subscriber identity information for the user's business telephone number. Alternatively, or in addition, one of the SIMs can be used primarily for voice calls with the other one can be used primarily for data transfers. Dual SIM or multi SIM UE devices have been especially popular in more recently developing economies such as China.

One type of dual SIM UE is referred to as Dual SIM Dual Active (DSDA) and may contain multiple receiver (Rx) architectures. A DSDA UE is capable of using two SIMs and two radios, so as to maintain two active sets of data communication simultaneously, e.g., the UE may be conducting a voice call using one SIM while performing data communication (e.g., Internet browsing) on the second SIM.

Another type of dual SIM UE may have only a single Rx architecture (e.g., for cost savings and reduced size requirements) and may be referred to as Dual SIM Dual Standby (DSDS). In a UE which contains only a single receiver, only one SIM may be in operation at any given time. Thus when the UE is utilizing a first SIM for a voice call, the second SIM will be idle. In some instances, when a SIM is currently in use and the UE detects initiation of a higher priority activity which requires the other SIM, the UE may suspend activity on the first SIM in order to undertake the higher priority activity on the other SIM. In a UE having multiple SIM devices and only one radio, the UE may encounter network problems when a SIM suspends and then subsequently resumes a radio resource control (RRC) connection with the network Accordingly, improvements in wireless communications, and in particular with respect to multiple subscriber identity functionality, would be desirable.

SUMMARY

In light of the foregoing and other concerns, it would be desirable to expand the functionality of wireless devices with respect to subscriber identities. In particular, it would be desirable to provide improved state synchronization between the wireless device and the network in an energy-efficient manner. The present disclosure relates to such techniques for facilitating state synchronization according to various embodiments.

Embodiments of the disclosure may thus be directed to methods for state synchronization in a dual-SIM dual-standby (DSDS) UE device, to a UE device configured to implement such a method, and/or to a non-transitory computer accessible memory medium storing program instructions executable by a processor to implement such a method. The UE device may include a radio (e.g., including one or more antennas and/or other radio components) for performing wireless communication. The UE device may also include a processing element configured to implement part or all of the method (e.g., by executing program instructions). The UE device may further include one or more user interface elements, such as a display. In addition, the UE device may include a non-transitory computer accessible memory medium, which may store program instructions executable by the UE.

In some embodiments, a DSDS UE is configured with a first SIM and a second SIM. The UE performs communications with a first cellular network using the first SIM and a first radio resource control (RRC) connection, and receives a request to perform a higher priority communication using the second SIM. In response to the request to perform the higher priority communication, the UE transmits a request to the first network to suspend the first RRC connection. After transmission of the request to suspend the first RRC connection, the UE receives a message from the first network to place the first RRC connection in an inactive state, and initiates a timer, wherein the timer is used to determine whether the first RRC connection remains in the inactive state or transitions to an idle state.

BRIEF DESCRIPTION OF THE DRAWINGS

A better understanding of the present subject matter can be obtained when the following detailed description of the preferred embodiment is considered in conjunction with the following drawings, in which.

Figure 1:
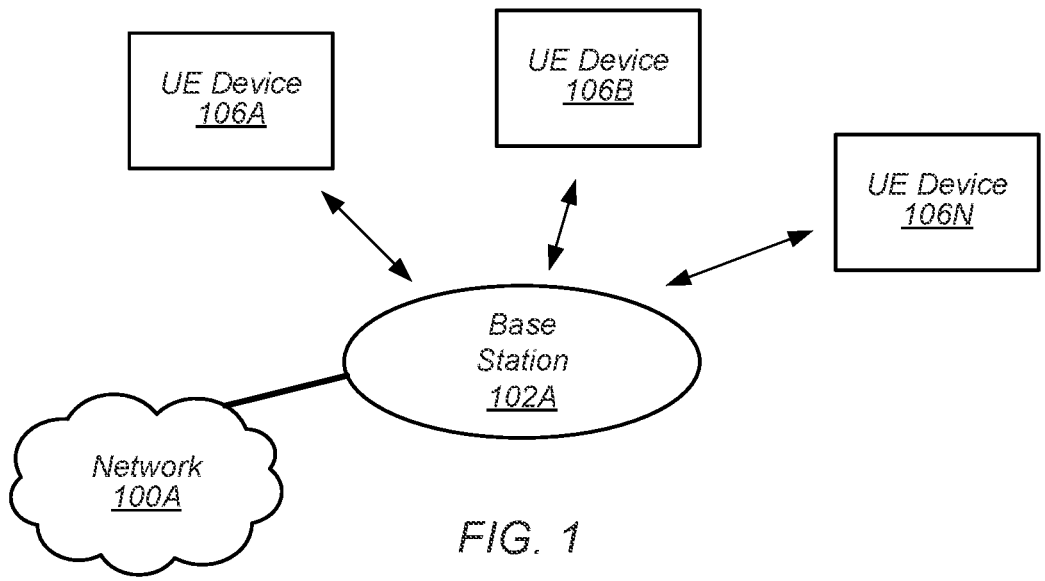
FIGS. 1-2 illustrate exemplary wireless communication systems between UE devices and one or more networks through one or more base stations, according to some embodiments.

While the features described herein are susceptible to various modifications and alternative forms, specific embodiments thereof are shown by way of example in the drawings and are herein described in detail. It should be understood, however, that the drawings and detailed description thereto are not intended to be limiting to the particular form disclosed, but on the contrary, the intention is to cover all modifications, equivalents and alternatives falling within the spirit and scope of the subject matter as defined by the appended claims.

DETAILED DESCRIPTION OF THE EMBODIMENTS

Acronyms

The following acronyms are used in this disclosure.
3GPP: Third Generation Partnership Project
3GPP2: Third Generation Partnership Project 2
GSM: Global System for Mobile Communications
UMTS: Universal Mobile Telecommunications System
LTE: Long Term Evolution
LTE-A: LTE-Advanced
SIM: Subscriber Identity Module
eSIM: Embedded SIM
IMSI: International Mobile Subscriber Identity
MCC: Mobile Country Code
MNC: Mobile Network Code Terms The following is a glossary of terms used in this disclosure:

Memory Medium—Any of various types of memory devices or storage devices. The term "memory medium" is intended to include an installation medium, e.g., a CD-ROM, floppy disks, or tape device; a computer system memory or random access memory such as DRAM, DDR RAM, SRAM, EDO RAM, Rambus RAM, etc.; a non-volatile memory such as a Flash, magnetic media, e.g., a hard drive, or optical storage; registers, or other similar types of memory elements, etc. The memory medium may include other types of memory as well or combinations thereof. In addition, the memory medium may be located in a first computer system in which the programs are executed, or may be located in a second different computer system which connects to the first computer system over a network, such as the Internet. In the latter instance, the second computer system may provide program instructions to the first computer for execution. The term "memory medium" may include two or more memory mediums which may reside in different locations, e.g., in different computer systems that are connected over a network. The memory medium may store program instructions (e.g., embodied as computer programs) that may be executed by one or more processors.

Carrier Medium—a memory medium as described above, as well as a physical transmission medium, such as a bus, network, and/or other physical transmission medium that conveys signals such as electrical, electromagnetic, or digital signals.

Programmable Hardware Element—includes various hardware devices comprising multiple programmable function blocks connected via a programmable interconnect. Examples include FPGAs (Field Programmable Gate Arrays), PLDs (Programmable Logic Devices), FPOAs (Field Programmable Object Arrays), and CPLDs (Complex PLDs). The programmable function blocks may range from fine grained (combinatorial logic or look up tables) to coarse grained (arithmetic logic units or processor cores). A programmable hardware element may also be referred to as "reconfigurable logic".

Computer System—any of various types of computing or processing systems, including a personal computer system (PC), mainframe computer system, workstation, network appliance, Internet appliance, personal digital assistant (PDA), personal communication device, smart phone, television system, grid computing system, or other device or combinations of devices. In general, the term "computer system" can be broadly defined to encompass any device (or combination of devices) having at least one processor that executes instructions from a memory medium.

User Equipment (UE) (or "UE Device")—any of various types of computer systems devices which are mobile or portable and which performs wireless communications. Examples of UE devices include mobile telephones or smart phones (e.g., iPhone™, Android™-based phones), wearable devices (e.g., smart watch, smart glasses), portable gaming devices (e.g., Nintendo DS™, PlayStation Portable™ Gameboy Advance™, iPhone™), laptops, PDAs, portable Internet devices, music players, data storage devices, or other handheld devices, etc. In general, the term "UE" or "UE device" can be broadly defined to encompass any electronic, computing, and/or telecommunications device (or combination of devices) which is easily transported by a user and capable of wireless communication.

Base Station—The term "Base Station" has the full breadth of its ordinary meaning, and at least includes a wireless communication station installed at a fixed location and used to communicate as part of a wireless telephone system or radio system.

Processing Element—refers to various elements or combinations of elements. Processing elements include, for example, circuits such as an ASIC (Application Specific Integrated Circuit), portions or circuits of individual processor cores, entire processor cores, individual processors, programmable hardware devices such as a field programmable gate array (FPGA), and/or larger portions of systems that include multiple processors.

Automatically—refers to an action or operation performed by a computer system (e.g., software executed by the computer system) or device (e.g., circuitry, programmable hardware elements, ASICs, etc.), without user input directly specifying or performing the action or operation. Thus the term "automatically" is in contrast to an operation being manually performed or specified by the user, where the user provides input to directly perform the operation. An automatic procedure may be initiated by input provided by the user, but the subsequent actions that are performed "automatically" are not specified by the user, i.e., are not performed "manually", where the user specifies each action to perform. For example, a user filling out an electronic form by selecting each field and providing input specifying information (e.g., by typing information, selecting check boxes, radio selections, etc.) is filling out the form manually, even though the computer system must update the form in response to the user actions. The form may be automatically filled out by the computer system where the computer system (e.g., software executing on the computer system) analyzes the fields of the form and fills in the form without any user input specifying the answers to the fields. As indicated above, the user may invoke the automatic filling of the form, but is not involved in the actual filling of the form (e.g., the user is not manually specifying answers to fields but rather they are being automatically completed). The present specification provides various examples of operations being automatically performed in response to actions the user has taken.

Figure 2:
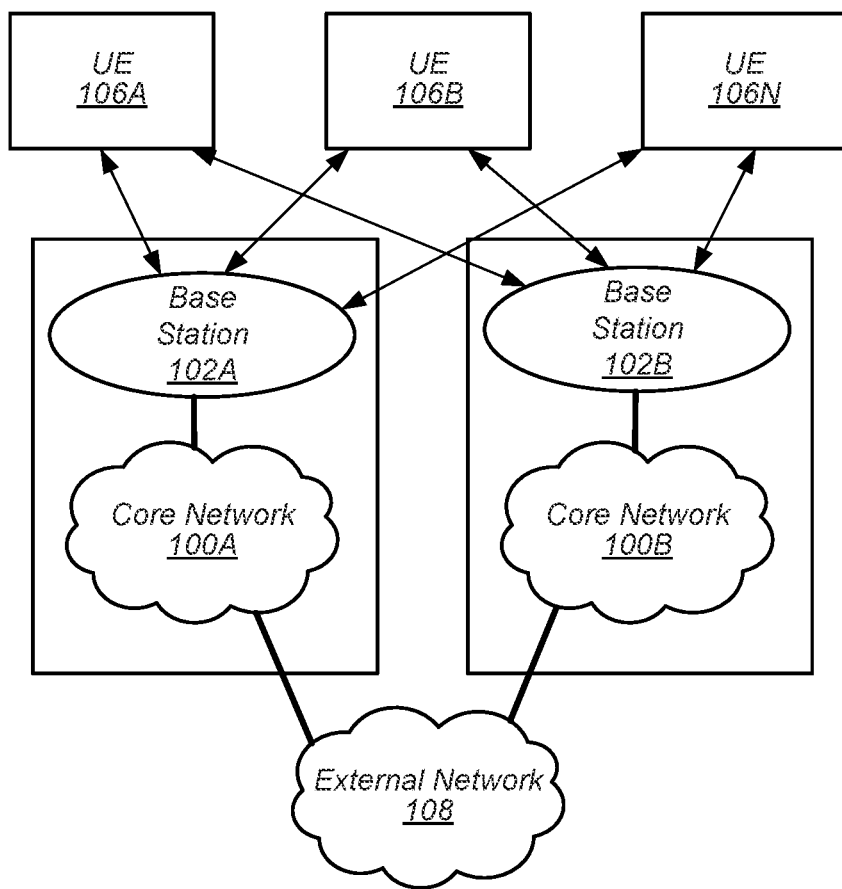
Figure 3:
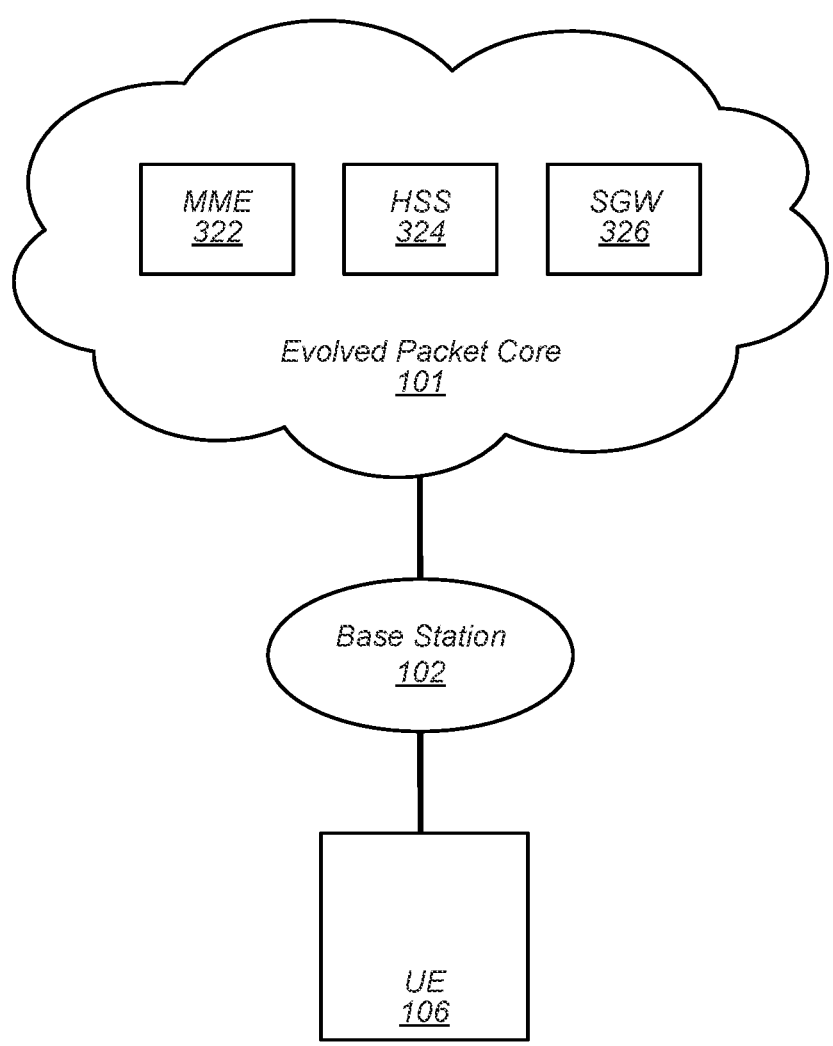
FIG. 3 illustrates an example cellular network system including an evolved packet core (EPC), according to some embodiments.

FIGS. 1-3—Communication System

FIGS. 1 and 2 illustrate exemplary (and simplified) wireless communication systems. It is noted that the systems of FIGS. 1 and 2 are merely examples of certain possible systems, and embodiments may be implemented in any of various systems, as desired.

The exemplary wireless communication system of FIG. 1 includes a base station 102A which communicates over a transmission medium with one or more user equipment (UE) devices 106A, 106B, etc., through 106N. Each of the user equipment devices may be referred to herein as a "user equipment" (UE). In the exemplary wireless communication system of FIG. 2, in addition to the base station 102A, base station 102B also (e.g., simultaneously or concurrently) communicates over a transmission medium with the UE devices 106A, 106B, etc., through 106N.

The base stations 102A and 102B may be base transceiver stations (BTSs) or cell sites, and may include hardware that enables wireless communication with the user devices 106A through 106N. Each base station 102 may also be equipped to communicate with a core network 100 (base station 102A may be coupled to core network 100A, while base station 102B may be coupled to core network 100B), which may be a core network of a cellular service provider. Each core network 100 may also be coupled to one or more external networks (such as external network 108), which may include the Internet, a Public Switched Telephone Network (PSTN), or any other network. Thus, the base station 102A may facilitate communication between the user devices and/or between the user devices and the network 100A; in the exemplary system of FIG. 2, the base station 102B may also facilitate communication between the user devices and/or between the user devices and the network 100B.

The base stations 102A and 102B and the user devices may be configured to communicate over the transmission medium using any of various radio access technologies (RATs), also referred to as wireless communication technologies, or telecommunication standards, such as GSM, UMTS (WCDMA), LTE, LTE-Advanced (LTE-A), 3GPP2 CDMA2000 (e.g., 1×RTT, 1×EV-DO, HRPD, eHRPD), Wi-Fi, WiMAX etc.

For example, base station 102A and core network 100A may operate according to a first cellular communication standard (e.g., LTE) while base station 102B and core network 100B operate according to a second (e.g., different) cellular communication standard (e.g., GSM, UMTS, and/or one or more CDMA2000 cellular communication standards). The two networks may be controlled by the same network operator (e.g., cellular service provider or "carrier"), or by different network operators. In addition, the two networks may be operated independently of one another (e.g., if they operate according to different cellular communication standards), or may be operated in a somewhat coupled or tightly coupled manner.

Note also that while two different networks may be used to support two different cellular communication technologies, such as illustrated in the exemplary network configuration shown in FIG. 2, other network configurations implementing multiple cellular communication technologies are also possible. As one example, base stations 102A and 102B might operate according to different cellular communication standards but couple to the same core network. As another example, multi-mode base stations capable of simultaneously supporting different cellular communication technologies (e.g., LTE and CDMA 1×RTT, GSM and UMTS, or any other combination of cellular communication technologies) might be coupled to a core network that also supports the different cellular communication technologies. Any of various other network deployment scenarios are also possible.

As a further possibility, it is also possible that base station 102A and base station 102B may operate according to the same wireless communication technology (or an overlapping set of wireless communication technologies). For example, base station 102A and core network 100A may be operated by one cellular service provider independently of base station 102B and core network 100B, which may be operated by a different (e.g., competing) cellular service provider. Thus in this case, despite utilizing similar and possibly compatible cellular communication technologies, the UE devices 106A-106N might communicate with the base stations 102A-102B independently, possibly by utilizing separate subscriber identities to communicate with different carriers' networks.

A UE 106 may be capable of communicating using multiple wireless communication standards. For example, a UE 106 might be configured to communicate using either or both of a 3GPP cellular communication standard (such as LTE) or a 3GPP2 cellular communication standard (such as a cellular communication standard in the CDMA2000 family of cellular communication standards). As another example, a UE 106 might be configured to communicate using different 3GPP cellular communication standards (such as two or more of GSM, UMTS, LTE, or LTE-A). Thus, as noted above, a UE 106 might be configured to communicate with base station 102A (and/or other base stations) according to a first cellular communication standard (e.g., LTE) and might also be configured to communicate with base station 102B (and/or other base stations) according to a second cellular communication standard (e.g., one or more CDMA2000 cellular communication standards, UMTS, GSM, etc.).

Base stations 102A and 102B and other base stations operating according to the same or different cellular communication standards may thus be provided as one or more networks of cells, which may provide continuous or nearly continuous overlapping service to UEs 106A-106N and similar devices over a wide geographic area via one or more cellular communication standards.

A UE 106 might also or alternatively be configured to communicate using WLAN, Bluetooth, one or more global navigational satellite systems (GNSS, e.g., GPS or GLONASS), one and/or more mobile television broadcasting standards (e.g., ATSC-M/H or DVB-H), etc. Other combinations of wireless communication standards (including more than two wireless communication standards) are also possible.

The UE 106 may be a device with wireless network connectivity such as a mobile phone, a hand-held device, a computer or a tablet, or virtually any type of wireless device.

The UE may include a processor that is configured to execute program instructions stored in memory. The UE may perform any of the method embodiments described herein by executing such stored instructions. Alternatively, or in addition, the UE may include a programmable hardware element such as an FPGA (field-programmable gate array) that is configured to perform any of the method embodiments described herein, or any portion of any of the method embodiments described herein.

The UE 106 may be configured to communicate using any of multiple wireless communication protocols. For example, the UE 106 may be configured to communicate using two or more of GSM, UMTS (W-DCMA, TD-SCDMA, etc.), CDMA2000 (1xRTT, 1xEV-DO, HRPD, eHRPD, etc.), LTE, LTE-A, WLAN, or GNSS. Other combinations of wireless communication standards are also possible.

The UE 106 may include one or more antennas for communicating using one or more wireless communication protocols. The UE 106 may share one or more parts of a receive and/or transmit chain between multiple wireless communication standards; for example, the UE 106 might be configured to communicate using either (or both) of GSM or LTE using a single shared radio. The shared radio may include a single antenna, or may include multiple antennas (e.g., for MIMO) for performing wireless communications.

FIG. 3—Example Cellular Network

FIG. 3 illustrates a simplified block diagram of an example cellular network (wireless communication system) that may be particularly useful for implementing various of the embodiments described herein. The UE 106 may be in communication with a cellular network, where the cellular network may comprise a base station 102 (or eNodeB) and an evolved packet core (EPC) 101, as shown. The UE 106 may communicate in a wireless manner with the base station 102. In turn, the base station 102 may be coupled to a core network, shown in this example embodiment as an evolved packet core (EPC) 101. As shown, the EPC 101 may include mobility management entity (MME) 322, home subscriber server (HSS) 324, and serving gateway (SGW) 326. The EPC 100 may include various other devices known to those skilled in the art as well.

Operations described herein as being performed by the cellular network (or NW) may be performed by one or more of the cellular network devices shown in FIG. 3, such as one or more of base station, 102, MME 322, HSS 324, or SGW 326 in EPC 100, among possible others.

Figure 4:
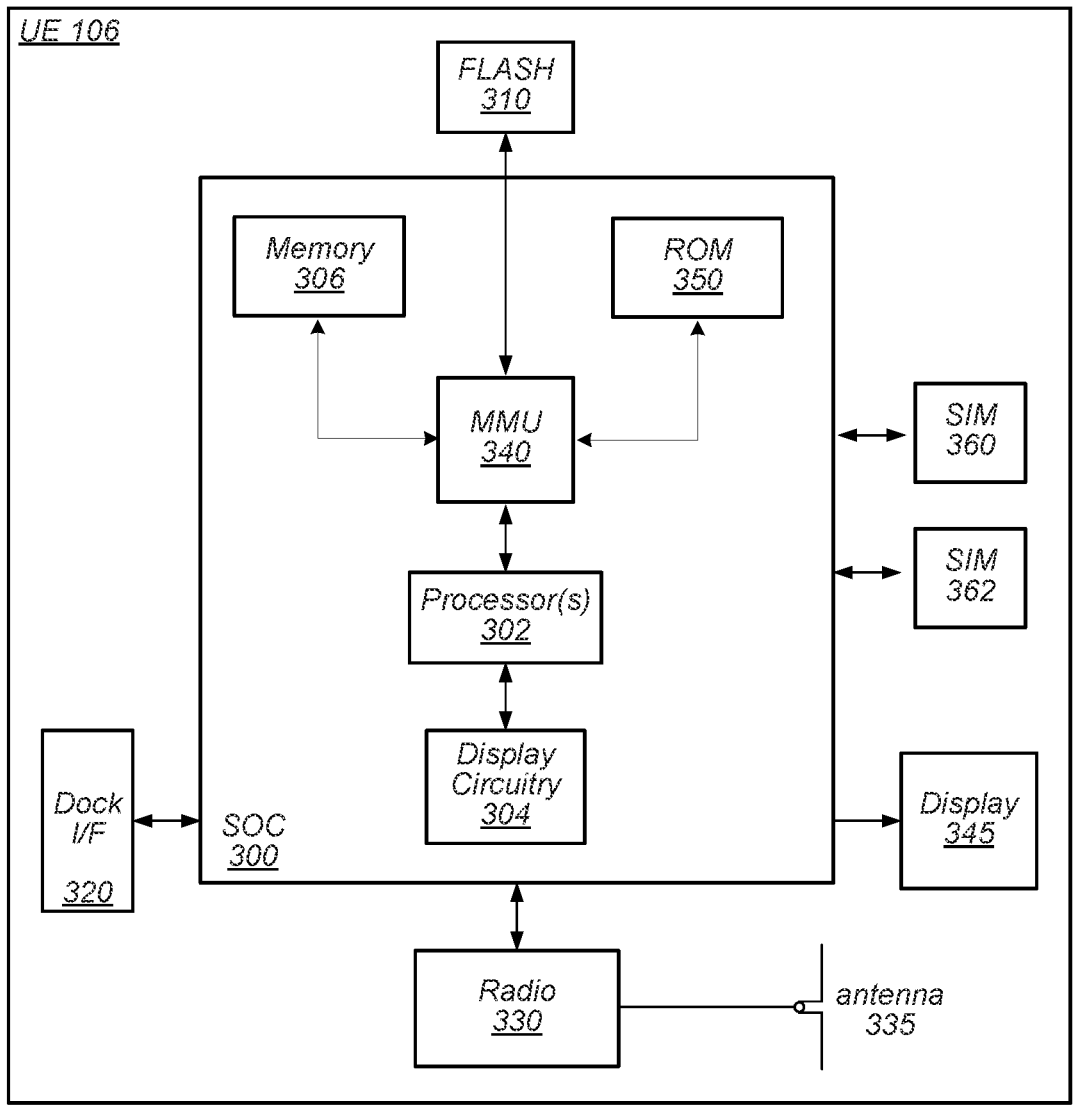
FIG. 4 illustrates an example block diagram of a user equipment device.

FIG. 4—Example Block Diagram of a UE

FIG. 4 illustrates an exemplary block diagram of a UE 106. As shown, the UE 106 may include a system on chip (SOC) 300, which may include portions for various purposes. For example, as shown, the SOC 300 may include processor(s) 302 which may execute program instructions for the UE 106 and display circuitry 304 which may perform graphics processing and provide display signals to the display 345. The processor(s) 302 may also be coupled to memory management unit (MMU) 340, which may be configured to receive addresses from the processor(s) 302 and translate those addresses to locations in memory (e.g., memory 306, read only memory (ROM) 350, NAND flash memory 310) and/or to other circuits or devices, such as the display circuitry 304, radio 330, connector I/F 320, and/or display 345. The MMU 340 may be configured to perform memory protection and page table translation or set up. In some embodiments, the MMU 340 may be included as a portion of the processor(s) 302.

As shown, the SOC 300 may be coupled to various other circuits of the UE 106. For example, the UE 106 may include various types of memory (e.g., including Flash memory 310), a connector interface 320 (e.g., for coupling to a computer system, dock, charging station, etc.), the display 345, and wireless communication circuitry 330 (e.g., for GSM, UMTS, LTE, LTE-A, CDMA2000, Bluetooth, Wi-Fi, GPS, etc.).

The UE device 106 may include at least one antenna, and possibly multiple antennas, for performing wireless communication with base stations and/or other devices. For example, the UE device 106 may use antenna 335 to perform the wireless communication. As noted above, the UE may be configured to communicate wirelessly using multiple wireless communication standards.

The UE 106 may also include one or more user interface elements. The user interface elements may include any of various elements, such as display 345 (which may be a touchscreen display), a keyboard (which may be a discrete keyboard or may be implemented as part of a touchscreen display), a mouse, a microphone and/or speakers, one or more cameras, one or more buttons, sliders, and/or dials, and/or any of various other elements capable of providing information to a user and/or receiving/interpreting user input.

As shown, the UE 106 may also include two or more subscriber identity modules (SIMs) 360 and 362. One or both of SIMs 360 and 362 may be implemented as an embedded SIM (eSIM). In this case, the SIMs 360 and/or 362 may be implemented in device hardware and/or software. For example, in some embodiments, the UE 106 may include an embedded UICC (eUICC), e.g., a device which is built into the UE 106 and is not removable. The eUICC may be programmable, such that one or more eSIMs may be implemented on the eUICC. In other embodiments, the eSIM may be installed in UE 106 software, e.g., as program instructions stored on a memory medium (such as memory 306 or Flash 310) executing on a processor (such as processor 302) in the UE 106. As one example, a SIM 360 may be an application which executes on a Universal Integrated Circuit Card (UICC). Alternatively, or in addition, one or both of SIMs 360 and 362 may be implemented as removeable SIM cards.

Each SIM 360 or 362 may include a number of types of information, including personalized information specific to a user and/or device (e.g., personalized information), and information that is not specific to a user and/or device (e.g., common information). The personalized information may include user/unit specific data, for example information identifying the user/unit to their carrier's network, personalized authorization and/or security information, etc. Some or all of the personalized information may be used as a subscriber identity for the UE 106, for example in order to identify the UE 106 to a carrier's network and to obtain cellular service from the carrier.

As one example, the personalized information may include one or more International Mobile Subscriber Identity (IMSI) numbers. An IMSI may identify the subscriber to their carrier's network. The IMSI may, for example, be a number including the subscriber's "home" mobile country code (MCC) and mobile network code (MNC), as well as a Mobile Subscription Identification Number (MSIN) which is unique to the subscriber. The personalized information may also or alternatively include a personal identification number (PIN) (e.g., a code which the user may use to access their SIM), a personal unblocking code and/or personal unblocking key (PUC/PUK), and one or more authentication keys (K/Ki). Any of a variety of other personalized information may also or alternatively be used, as desired.

Thus, each SIM 360 and 362 may contain subscriber identity information that may be used to identify the UE 106 to its subscriber's carrier cellular network. As noted above, the UE 106 may utilize multiple subscriber identities. For example, a user may consider it desirable to obtain service from multiple carriers for any of a variety of reasons, including differing footprints/service areas of different carriers, different service plans/pricing offered by different carriers, or different technologies used. In some cases it may be desirable to utilize multiple subscriber identities (whether from the same or different carriers) as a means of differentiating types of interactions, such as work-related communications and personal communications.

As a further possibility, a situation might arise in which it might be desirable to utilize multiple subscriber identities in a single device for some carriers which implement LTE networks. In particular, in many cases an LTE (e.g., as a packet-switched communication technology) network may be (at least initially) deployed for data communications (e.g., web browsing, email and other networking applications, etc.), while a (e.g., pre-existing) GSM and/or UMTS (e.g., which may include circuit-switched communication technologies) network may be utilized provided for voice communications.

As further described below, the UE may implement various techniques which enable a particular SIM to perform suspend and resume operations with the cellular network while reducing disruption due to RRC state mismatch. Accordingly, as described further subsequently herein, the UE 106 may include hardware and software components for implementing methods for improved suspend/resume operations when transitioning between use of the different SIMs.

The processor 302 of the UE device 106 may be configured to implement part or all of the methods described herein, e.g., by executing program instructions stored on a memory medium (e.g., a non-transitory computer-readable memory medium). In other embodiments, processor 302 may be configured as a programmable hardware element, such as an FPGA (Field Programmable Gate Array), or as an ASIC (Application Specific Integrated Circuit).

Figure 5:
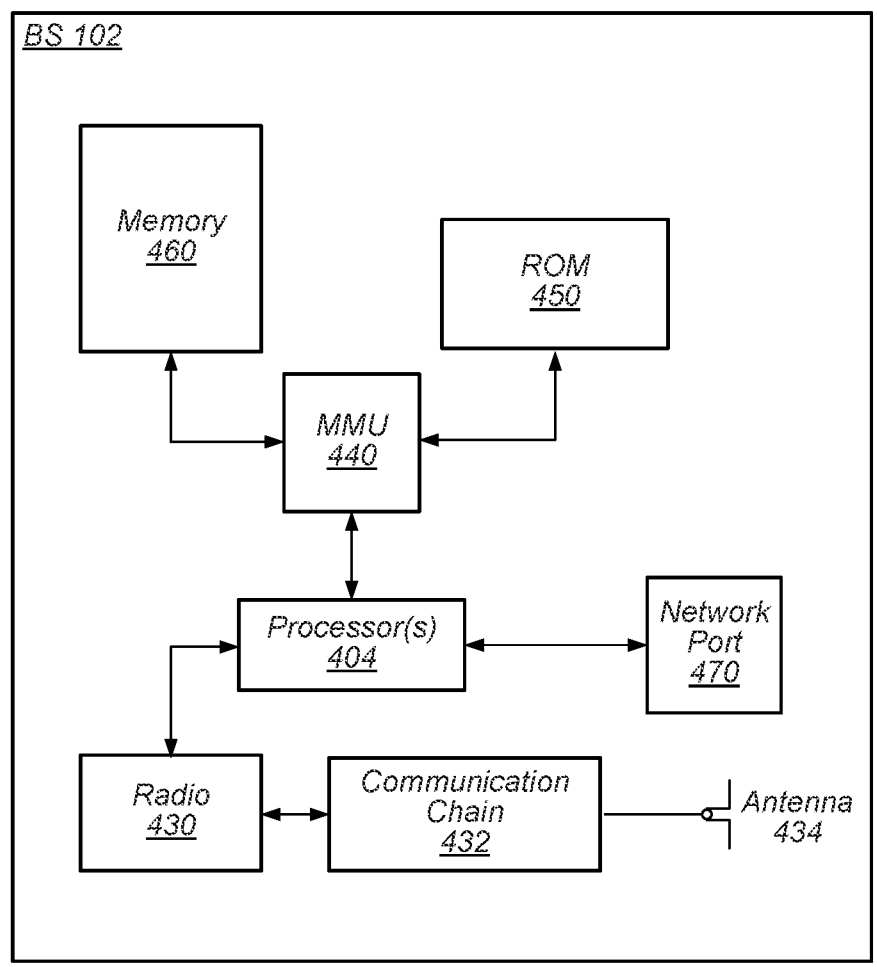
FIG. 5 illustrates an example block diagram of a base station.

FIG. 5—Exemplary Block Diagram of a Base Station

FIG. 5 illustrates an exemplary block diagram of a base station 102. It is noted that the base station of FIG. 5 is merely one example of a possible base station. As shown, the base station 102 may include processor(s) 404 which may execute program instructions for the base station 102. The processor(s) 404 may also be coupled to memory management unit (MMU) 440, which may be configured to receive addresses from the processor(s) 102 and translate those addresses to locations in memory (e.g., memory 460 and read only memory (ROM) 450) or to other circuits or devices.

The base station 102 may include at least one network port 470. The network port 470 may be configured to couple to a telephone network and provide a plurality of devices, such as UE devices 106, access to the telephone network as described above in FIGS. 1 and 2.

The network port 470 (or an additional network port) may also or alternatively be configured to couple to a cellular network, e.g., a core network of a cellular service provider. The core network may provide mobility related services and/or other services to a plurality of devices, such as UE devices 106. In some cases, the network port 470 may couple to a telephone network via the core network, and/or the core network may provide a telephone network (e.g., among other UE devices serviced by the cellular service provider).

The base station 102 may include at least one antenna 434, and possibly multiple antennas. The at least one antenna 434 may be configured to operate as a wireless transceiver and may be further configured to communicate with UE devices 106 via radio 430. The antenna 434 communicates with the radio 430 via communication chain 432. Communication chain 432 may be a receive chain, a transmit chain or both. The radio 430 may be configured to communicate via various wireless telecommunication standards, including, but not limited to, LTE, WCDMA, CDMA2000, etc.

The processor 404 of the base station 102 may be configured to implement part or all of the methods described herein, e.g., by executing program instructions stored on a memory medium (e.g., a non-transitory computer-readable memory medium). Alternatively, the processor 404 may be configured as a programmable hardware element, such as an FPGA (Field Programmable Gate Array), or as an ASIC (Application Specific Integrated Circuit), or a combination thereof.

The cellular network devices such as shown in FIG. 3 may have a somewhat similar architecture as described above, but would typically not include RF circuitry or an antenna. Thus each of the cellular network devices shown in FIG. 3 would typically have a processing element and memory for performing their respective functions.

As used herein, a network or cellular network (e.g., NW1 and/or NW2 as described below) may refer to one or more physical entities contained within a network infrastructure to perform the described methods. For example, a gNB (or eNB) such as that illustrated in FIG. 5 may directly receive indications and messaging from the UE and may relay these messages from the UE to an access and mobility management function (AMF) or a mobile management entity (MME) on the Core Network side. The MME (or AMF) may inform the gNB (or eNB) to retain the RRC context of the UE (i.e. a Connected state and/or an established EPS bearer/PDU session along with the QoS details), the MME (or AMF) may start the timer, and if the timer expires before the suspended SIM resumes, the MME (or AMF) may inform the serving gateway (S-GW) or the user plane function (UPF) to release the bearers/PDN contexts for UE as well as inform the eNB (or gNB) to release the UE context (i.e. to forget the C-RNTI and the rest of the state information of the UE and consider the UE to be IDLE). If the timer is running and the eNB (or gNB) gets an RRC resume request from the UE, then the eNB (or gNB) may confirm that the C-RNTI exists and that the UE context may be recovered and may forward the Resume request to the MME (or AMF), which may inform the S-GW (or UPF) to modify the radio bearer (e.g., if they had earlier told the S-GW or UPF to freeze their context), stop the timer, and/or continue as if the UE was connected. Said another way, the combination of eNB-MME-SGW for LTE or gNB-AMF-UPF for 5G NR may be understood as being interconnectedly involved in performing the embodiments described herein.

RRC State Mismatch Avoidance—Problem Statement

As described above, some UE devices may be capable of containing multiple subscriber identity modules, or SIMs. In some cases, these SIMs may be Universal SIMs, or USIMs.

Some UE devices with multiple SIMs, i.e., dual-SIM and multi-SIM devices, including multi-USIM (or MUSIM) devices, may have a singular receiver (RX) architecture. In other words, some multi-SIM UEs may each have only one receiver system for conducting cellular communications for their multiple SIMs. Thus in this instance the multiple SIMs on the UE share the single receiver system (or single radio). For these multi-SIM UEs, it may become necessary for the UE to suspend activity on one SIM while undertaking another higher-priority activity on another SIM.

For example, the UE 106 may be a dual-SIM device, i.e., may contain two SIMs, and may have a single receiver system for the two SIMs. The first SIM may be configured with a preference for data transfer, and the second SIM may be configured with a preference for non-data communications, e.g., for circuit-switched (CS) communications, or cellular voice calls.

In a common scenario, the first SIM, i.e., the data SIM, may be engaged in data communications and may be operating in a Connected mode with the network, e.g., via a first radio resource control (RRC) connection. For example, the UE may be actively performing data transfer using the first SIM via the first RRC connection, e.g., for one or more applications on the UE, such as an Internet browsing application and/or one or more background applications. In this scenario, the second SIM, i.e. the non-data SIM instance, may be operating in Idle mode.

The UE may then receive a page or user input indicating a higher-priority communication to be conducted via the second SIM. For example, the UE may receive a mobile terminated (MT) voice call from the network, a user of the UE may initiate a mobile originated (MO) voice call, or the UE may receive or send an SMS (Short Message Service) message or other circuit-switched (CS) communication.

In response to the indication for higher-priority communication on the second SIM, the UE may perform a local suspension of the first RRC connection of the first SIM, i.e., may suspend data communications on the first SIM, in order to make the UE's receiver available to conduct the higher-priority communication on the second SIM.

When the higher-priority communication on the second SIM is completed (e.g., in the case of a voice call, because the user terminated the call), the second SIM may return to Idle mode. The UE may then operate to resume the previously suspended first RRC connection using the first SIM.

Problems may arise at this point if the network is no longer synchronized with the UE regarding the state of the first RRC connection.

The resumption of the suspended first RRC connection may be performed according to a resumption sequence, e.g. via an RRC Connection Reestablishment request. In some cases, this resumption sequence may not be in synchronization with the network, which may have developed an incompatible perception of the first RRC connection after the first RRC connection was suspended. This lack of synchronization may impact the throughput performance on the first SIM, and may lead to missed paging messages during resumption and re-establishment procedures.

In some cases, the network may not have received an appropriate indication that the first SIM had transitioned into Idle mode (when the UE earlier suspended communication on the first SIM), and hence may be unprepared for the resumption sequence.

In one set of undesirable scenarios, the network may contain obsolete information indicating that the first SIM is still in its original Connected mode, even after the first SIM has transitioned into Idle mode. Hence, the network may attempt to page the UE on the first SIM, e.g., for an MT voice call, even though the UE is in Idle mode. This can result in missed pages and/or dropped or failed calls. The network may also be wasting network resources such as uplink and downlink resources by allocating them to the first RRC connection (i.e., the first SIM on the UE), even though the first RRC connection is inactive and hence unable or unprepared to receive these communications.

In a second set of undesirable scenarios, the network may have dropped the first RRC connection with the first SIM at some point after the first SIM (i.e., the first RRC connection) transitioned to Idle mode. If the first SIM attempts to re-establish the first RRC connection in order to perform or resume certain data communications, the network may then be unable to receive its communications. The UE may then need to perform procedures to establish a new connection with the network in order to perform these communications. Thus, the first SIM may be unable to promptly resume data communications via the first RRC connection. This may lead to data transfer failures and long delays (increased latency) for the user of the UE.

Producers and vendors of multi-SIM and MUSIM devices have implemented various proprietary solutions to handle some of these above-mentioned scenarios and associated problems. However, these solutions must be validated across and adjusted for many different deployments around the world in order to ensure adequate performance, which may demand a considerable amount of effort and resources. Therefore, improvements in the field are desired. In particular, a 3GPP-defined solution would be desirable to address these and other problems.

UE Indicates Suspend/Renewal Operations to the Network for RRC State Synchronization In some embodiments, in a scenario such as that described above where a first SIM is suspended so that a second SIM can perform a higher priority task, the first SIM which is being suspended (or the software stack executing and using the first SIM) can gracefully indicate to the NW using a "lightweight" mechanism (a relatively minor amount of signaling", that it being suspended for another high priority activity on the other SIM instance Alternatively, during resumption when the second SIM has completed the higher priority task and relinquished use of the radio, and the first SIM is resuming a Connected state to resume its data transfers, the first SIM that is requesting resumption could inform the cellular network at that time that this resumption is after a local suspension due to a high priority activity on the other SIM instance.

One motivation or goal in performing the above method is to avoid RRC state mismatch between the UE and the network, and more particularly, between both the first and second SIMs and their respective cellular networks.

In one embodiment, the first SIM which is about to be suspended can request for a temporary transition to the RRC Inactive state, and the connection state or context of the SIM is stored and maintained at the network side while the other high priority activity is completed on the first SIM. The connection state or context of the first SIM is stored and maintained at the network side so that the network can quickly restore the connection state of the first SIM when the second SIM completes its higher priority task.

For example, in storing the UE context, we may refer to herein that the NW may store one or more of a UE identifier such as the UE ID (i.e. C-RNTI); a state the UE was in (e.g., Connected); a time when the SIM1 was suspended; and/or packet data networks (PDNs), evolved packet system (EPS) bearers, and/or packet data unit (PDU) sessions that were established when the UE was in Connected mode and their quality of service (QoS) and/or QoS Flow Identifier (QFI) thereof. Using this stored information, when the SIM1 connection is resumed, the NW may allocate the physical and transport channel resources to the UE for the PDN/EPS bearer/PDU sessions and for the QoS/QFI configured earlier and may resume the data transfer.

The conveyance or communication of information regarding SIM suspension/resumption between the UE and the cellular network may result in less paging failures on the suspended SIM, since the network is now aware of the suspension status of the SIM. Further, these methods provide for a faster and more efficient resumption of the suspended SIM with a reduced chance of the network rejecting the resumption due to a potential RRC state mismatch, These methods are described in greater detail below.

Figure 6:
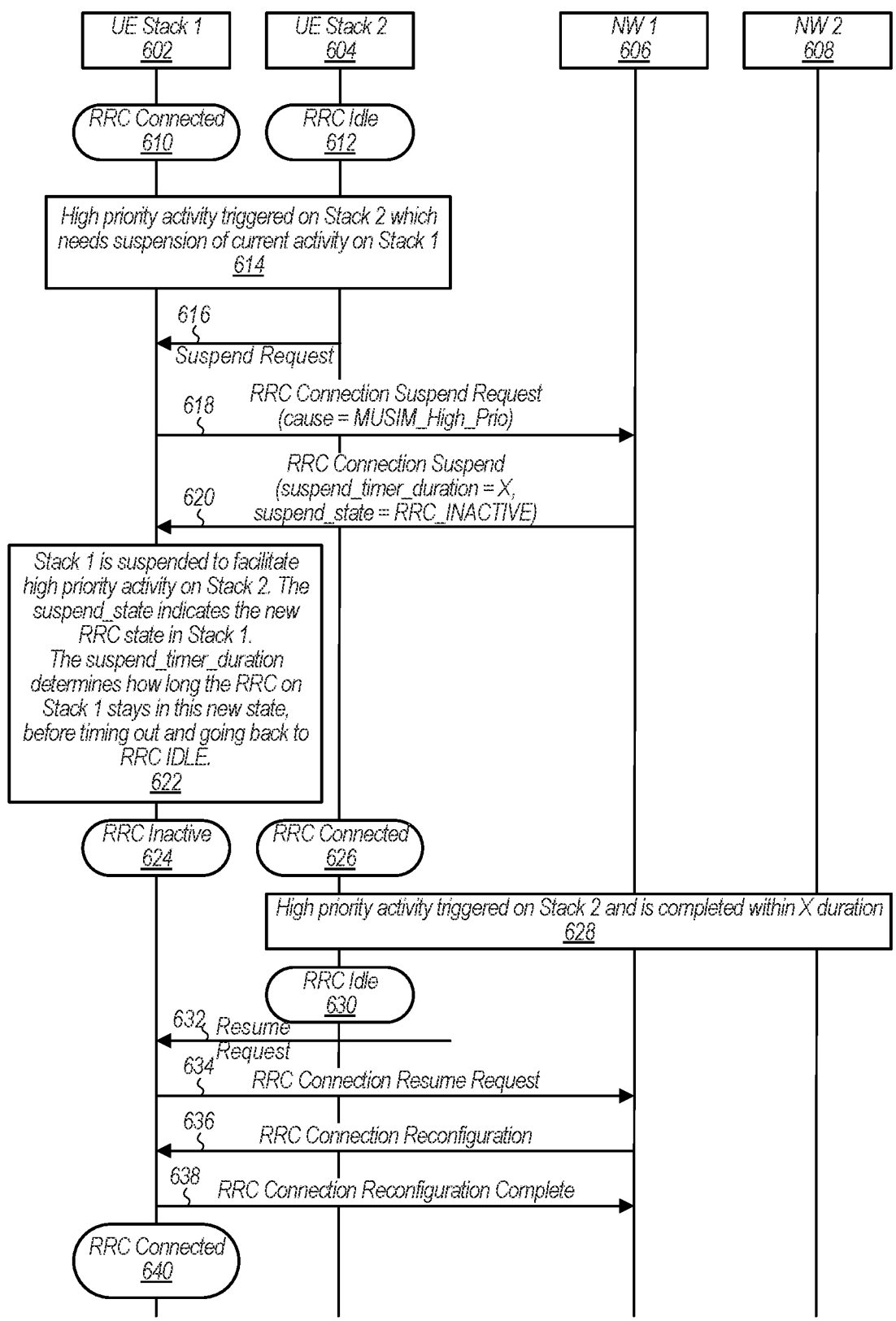
FIG. 6 is a message sequence chart illustrating an example method where the UE provides information to the network regarding suspend/resume operations to maintain RRC state synchronization, where resumption occurs without a timeout event, according to some embodiments.

FIG. 6—UE Provides Indications to the Network for RRC State Synchronization (Resume without Timeout)

FIG. 6 is a message sequence chart illustrating a method for UE with two SIMs to coordinate with the network (or provide indications to the network) regarding its SIM suspend/resume operations for improved RRC state synchronization.

The message sequence chart of FIG. 6 illustrates the various messaging between a first communication software stack (UE Stack 1, 602) operating with a first SIM, a second communication software stack (UE Stack 2, 604) operating with a second SIM, a first cellular network (NW 1, 606) and a second cellular network (NW 2, 608). The first communication software stack (UE Stack 1) operating with the first SIM may communicate with NW 1, and the second communication software stack (UE Stack 2) operating with the second SIM may communicate with NW 2. The term "communication software stack" refers to software executing on the UE which enables the UE to communicate with a network. In some embodiments, the UE maintains a communication software stack for each of the two SIMs, i.e., the UE maintains a first communication software stack that executes in conjunction with the first SIM (SIM 1) to perform cellular communication using the first SIM, and UE maintains a second communication software stack that executes in conjunction with the second SIM (SIM 1) to perform cellular communication using the second SIM.

As shown, at 610 UE Stack 1 may be in RRC Connected mode performing data transfers with NW 1 using the radio (RF) of the UE 106. NW 1 may also be in Connected mode since it is communicating with UE Stack 1. Since the UE contains only a single radio, when the radio is being used by UE Stack 1, then UE Stack 2 is in RRC Idle mode at 612.

At 614, a high priority activity is triggered on UE Stack 2, wherein this high priority activity triggered on UE Stack 2 requires suspension of current activity on UE Stack 1. For example, UE Stack 1 may be engaged in RRC Connected mode performing data transfers with NW 1, and a voice call may be activated on UE Stack 2. In other words, a voice call may be initiated (or received) by the UE, wherein the voice call is handled by UE Stack 2. For example, a mobile originating (MO) call may be made or placed by the user of the UE, where the MO call is handled using UE Stack 2. Alternatively, a mobile terminating (MT) call may be received by the UE, where the MT call is handled using UE Stack 2.

In response to this higher priority activity being initiated on UE Stack 2, at 616 UE Stack 2 may send a suspend request to UE Stack 1 to notify UE Stack 1 that it needs to suspend operations.

In response to the notification from UE Stack 2, at 618 UE Stack 1 may then transmit an RRC Connection Suspend Request to the cellular network to which UE Stack 1 is connected, (NW 1). The RRC Connection Suspend Request may comprise information that specifies the cause of the suspend request. More specifically, the RRC Connection Suspend Request may comprise information that specifies that the suspend request is due to a higher priority activity being initiated on another SIM of the UE. The cause information may take the form of a code, such as "MUSIM_High_Priority" or something similar.

As shown, receipt of the RRC Connection Suspend Request from UE Stack 1 may cause the NW 1 to transmit an RRC Connection Suspend message at 620 back to UE Stack 1. The RRC Connection Suspend message may include a code or instruction that specifies that UE Stack 1 should transition from Connected mode to Inactive mode. This code or instruction may take the form of "suspend_state=RRC_INACTIVE" or something similar. The presence of this code in the RRC Connection Suspend message instructs UE Stack 1 to enter the Inactive state. In other words, the "suspend_state" code is used to indicate the new RRC state for UE Stack 1.

The RRC Connection Suspend message may also include a code or instruction that specifies a timer duration for a suspend timer operating on the UE. This code or instruction may take the form of "suspend_timer_duration=X". As discussed further below, the suspend timer duration may specify an amount of time during which the UE Stack 1 will remain in RRC Inactive mode before transitioning to RRC Idle mode. Typical values for the suspend timer duration may range from several minutes or seconds to several hours.

In response to UE Stack 1 receiving the RRC Connection Suspend message from NW 1, UE Stack 1 is suspended at 622 and thus UE Stack 1 may enter RRC Inactive mode at 624 to facilitate or enable the higher priority activity on UE Stack 2. Receipt of the RRC Connection Suspend message may also trigger the start of the suspend timer on the UE.

In some embodiments, NW 1 may also include a similar suspend timer, and transmission of the RRC Connection Suspend message may cause NW 1 to start its own suspend timer. Thus both UE Stack 1 (the UE) and NW 1 may start its own respective suspend timer to determine how long the RRC connection between UE Stack 1 and NW 1 remains in Inactive mode before timing out and transitioning to RRC Idle mode.

As shown, triggering of the high priority activity on UE Stack 2 causes UE Stack 2 to enter RRC Connected mode at 626. UE Stack 2 may then perform the higher priority activity at 628, e.g., a voice call.

In the exemplary embodiment of FIG. 6, the high priority activity on UE Stack 2 (the voice call) is completed at 628 before the suspend timer expires. Upon completion of the high priority activity on UE Stack 2, UE Stack 2 enters RRC Idle mode at 630. UE Stack 2 may then notify UE Stack 1 at 632 that the high priority activity on UE Stack 2 has been completed and UE Stack 2 is now in Idle mode. In response, UE Stack 1 may transmit an RRC Connection Resume Request at 634 to NW 1. NW 1 receives the RRC Connection Resume Request and in response transmits an RRC Connection Reconfiguration message at 636 back to UE Stack 1. UE Stack 1 receives the RRC Connection Reconfiguration message and in response enters RRC Connected mode. UE Stack 1 then transmits an RRC Connection Reconfiguration Complete message at 638 back to NW 1, thereby entering the RRC Connected mode.

Figure 7:
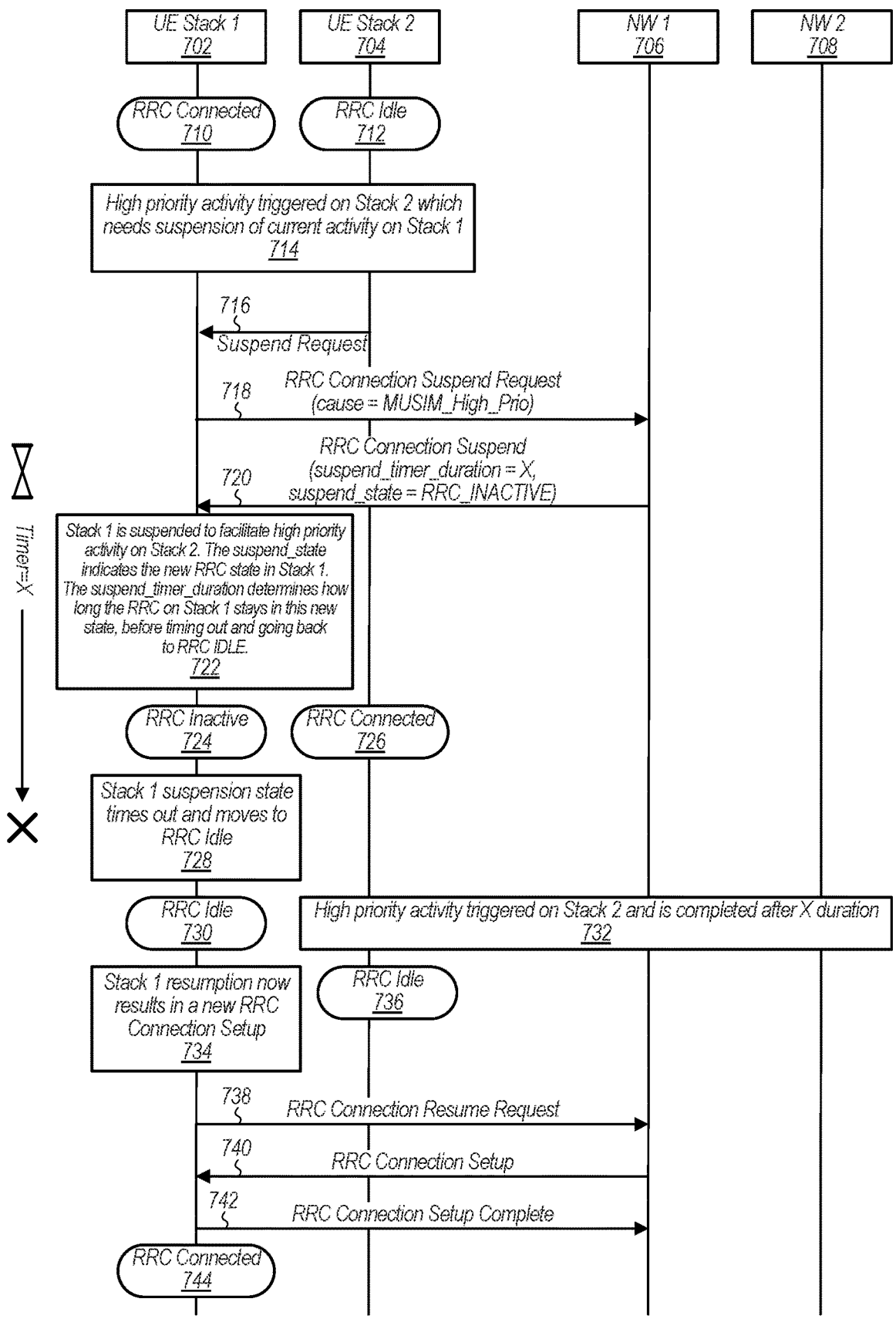
FIG. 7 is a message sequence chart illustrating an example method where the UE provides information to the network regarding suspend/resume operations to maintain RRC state synchronization, where resumption occurs with a timeout event, according to some embodiments.

FIG. 7—Message Flow Diagram—UE Provides indications to the Network for RRC State Synchronization (Resume with Timeout)

FIG. 7 is a message sequence chart illustrating a method for UE with two SIMs to coordinate with the network (or provide indications to the network) regarding its SIM suspend/resume operations for improved RRC state synchronization. Like FIG. 6, FIG. 7 describes communication between a UE Stack 1 702 and NW1 706, as well as communication between UE Stack 2 704 and NW2 708. FIG. 7 is similar to FIG. 6, except that FIG. 7 illustrates the case where the suspend timer expires prior to completion of the high priority activity over UE Stack 2. For example, each of steps 710-726 may proceed similarly to steps 610-626 of FIG. 6.

However, the procedure outlined in FIG. 7 differs from FIG. 6 beginning at step 728. Specifically, at 728, the suspension timer expires and UE Stack 1 enters an RRC Idle state at 730 prior to completion of the high priority activity over UE Stack 2 at 732.

Accordingly, at 734, UE Stack 1 may resume its connection with NW 1 at 734 by setting up a new RRC Connection. At 738, UE Stack 1 transmits an RRC Connection Resume Request to NW 1. At 740, NW 1 responds to UE Stack 1 with an RRC Connection Setup message, and UE Stack 1 subsequently responds to NW 1 at 742 with an RRC Connection Setup Complete message to enter the RRC Connected state with NW 1 at 744.

Figure 8:
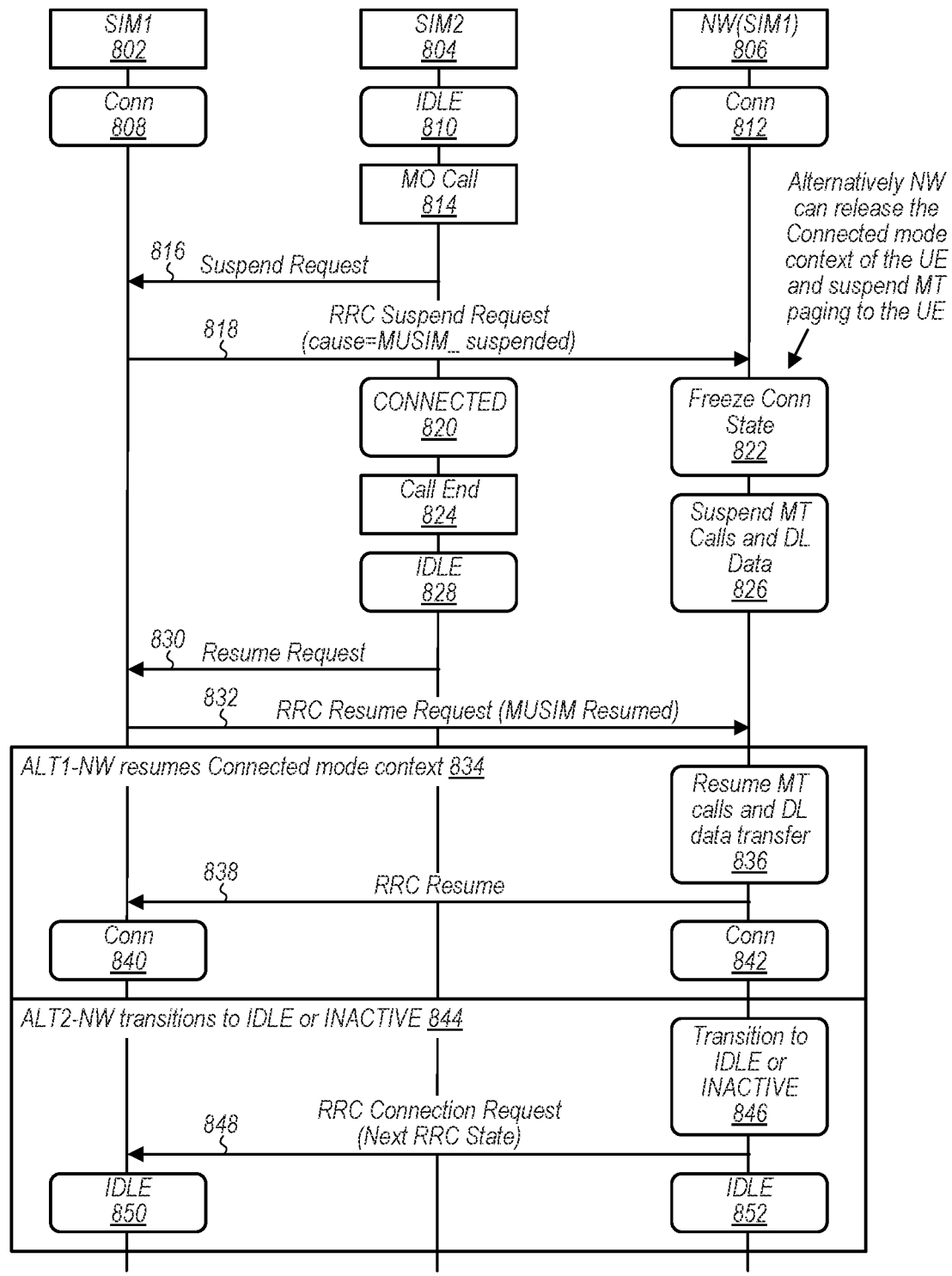
FIG. 8 is a message sequence chart illustrating an example method where the UE provides information to the network regarding suspend/resume operations and the network stores connected state information to maintain RRC state synchronization, according to some embodiments.

FIG. 8—Network Stores Connected State Context to Maintain Synchronous RRC States FIG. 8 is a message sequence chart which illustrates an alternative embodiment. Similar to FIGS. 6 and 7, the message sequence chart of FIG. 8 illustrates the various messaging between a first communication software stack operating with a first SIM (SIM1), 802, a second communication software stack operating with a second SIM (SIM2), 804, and the cellular network (NW (SIM1)) 806 communicating with the first SIM. The first communication software stack operating with SIM1 may be in Connected mode 808, 812, performing data transfers with NW (SIM1) using the radio (RF) of the UE 106. As shown, the Network NW (SIM1) is also in Connected mode since it is communicating with the first communication software stack. Since the UE contains only a single radio, when the radio is being used by SIM1 (used by the first communication software stack operating with SIM1), then SIM2 (the second communication software stack operating with SIM2) is in Idle mode 810. In the following discussion, the term "SIM1" is used to refer to the first communication software stack operating in conjunction with SIM1, and similarly "SIM2" is used to refer to the second communication software stack operating in conjunction with SIM2.

At 814, a voice call is initiated (or received) by SIM2. As shown in this example, a mobile originating (MO) call is made or placed by the user of the UE, where the MO call is performed using SIM2. In response to the MO call being initiated, SIM2 transmits a Suspend Request at 816 to SIM1. In response to the Suspend Request, SIM1 transmits an RRC Suspend Request at 818 to the cellular network to which SIM1 is connected, NW (SIM1). In the embodiments of FIGS. 6 and 7, receipt of a Suspend Request from SIM1 would cause the NW (SIM1) to transmit a suspend message back to SIM1, including a prescription for SIM1 to go to an inactive state and a timer duration value as described above. However, in the embodiment of FIG. 8, rather than transmitting such a suspend message back to the UE (SIM1), instead the network "freezes" the context (or connection state) of the current Connected mode of SIM1 at 822. In other words, the network NW (SIM1) stores the current Connected mode parameters/data relating to the context or connection state of SIM1 in memory and preserves this stored context for later use (in restoring Connected mode). In addition, in response to receipt of the Suspend Request from SIM1, the network also suspends or prevents mobile terminating (MT) calls and downlink data from being transferred to SIM1 at 826. In other words, since NW (SIM1) knows that SIM1 will not be reachable for a period of time, i.e., that SIM1 will not be able to receive communications for a period of time (because it is requesting to be suspended), NW (SIM1) configures itself such that it will not send any downlink notifications of paging to SIM1 for a period of time, and further that NW (SIM1) will not schedule any new data for SIM1. As an alternative to the above, e.g., if the network does not support this feature, the NW (SIM1) can send an RRC Connection Release message to SIM1 to place SIM1 in either the Inactive or Idle state, and suspend paging to SIM1, and the NW (SIM1) can also enter to a similar Inactive or Idle state.

In response to the MO call being made using SIM2, SIM2 enters a Connected state at 820, and a voice call is performed, which may involve a second different cellular network. At 824, the voice call being made using SIM2 ends, and SIM2 returns to an Idle state at 828. After the SIM2 goes back to an Idle state, SIM2 sends a Resume Request message to SIM1 at 830. In response to receiving the Resume Request from SIM1, SIM2 then sends an RRC Resume Request to NW (SIM1) at 832. The RRC Resume Request sent by SIM1 may contain information indicating that this is a resumption from a situation involving a higher priority connection that necessitated another SIM on the UE to assume control of the radio. When the network NW (SIM1) receives the RRC Resume Request from SIM1, the network may respond in one of a plurality of different manners.

In one embodiment, the NW (SIM1) may restored the connection state or context of the previous Connected mode connection at 834, i.e., the connection state that was previously "frozen" at step 822. This enables the previous Connected mode to "resume" from where it left off. The NW (SIM1) may also resume (or discontinue the suspension of) mobile terminating calls and downlink data transfers to SIM1. NW (SIM1) may also send an RRC Resume message to SIM1 at 838 to notify SIM1 that the prior Connected mode has been resumed. Thus in this embodiment, the NW (SIM1) and SIM1 may both return to Connected mode (Connected state) at 840 and 842, and data transfer, MT calls, and paging are now operational as they normally would be in Connected mode.

In another embodiment, it may be the case that a significant period of time may have elapsed during which the connection to SIM1 has been suspended. For example, the MO voice call performed by SIM2 may have lasted longer than a specified period of time (e.g., as determined by a timer used for this purpose). In this case, the NW (SIM1) may have discarded the stored Connected mode context upon the expiration of a timer (and then of course the network would no longer have stored Connected mode parameters to restore). In this instance, when this certain period of time has elapsed, the NW (SIM1) may transition to either Idle or Inactive mode at 844, 846, and discard (no longer store) the previously stored Connected mode context. The NW (SIM1) may also transmit an RRC Connection Release message to SIM1 at 848. This message may also indicate to SIM1 that it should transition to Idle mode as well, which it may perform at 850. In this case, a new connection may need to be reestablished between SIM1 and NW (SIM1) in order to enable data communication between them.

An important benefit to the above method is that this ensures that there is no discrepancy in the RRC states between the network and the UE. In addition, the network suspends paging and downlink data to the suspended SIM, thus preventing any problems associated with attempting to communicate with a suspended device. Further, the network maintains full control over the UE's RRC state, and thus the network ensures that both SIMs of the UE remain in synch with the RRC state of the network, i.e., that the RRC state of the SIMs matches that of the network at all times.

RRC State Mismatch in 5G NR

Figure 9:
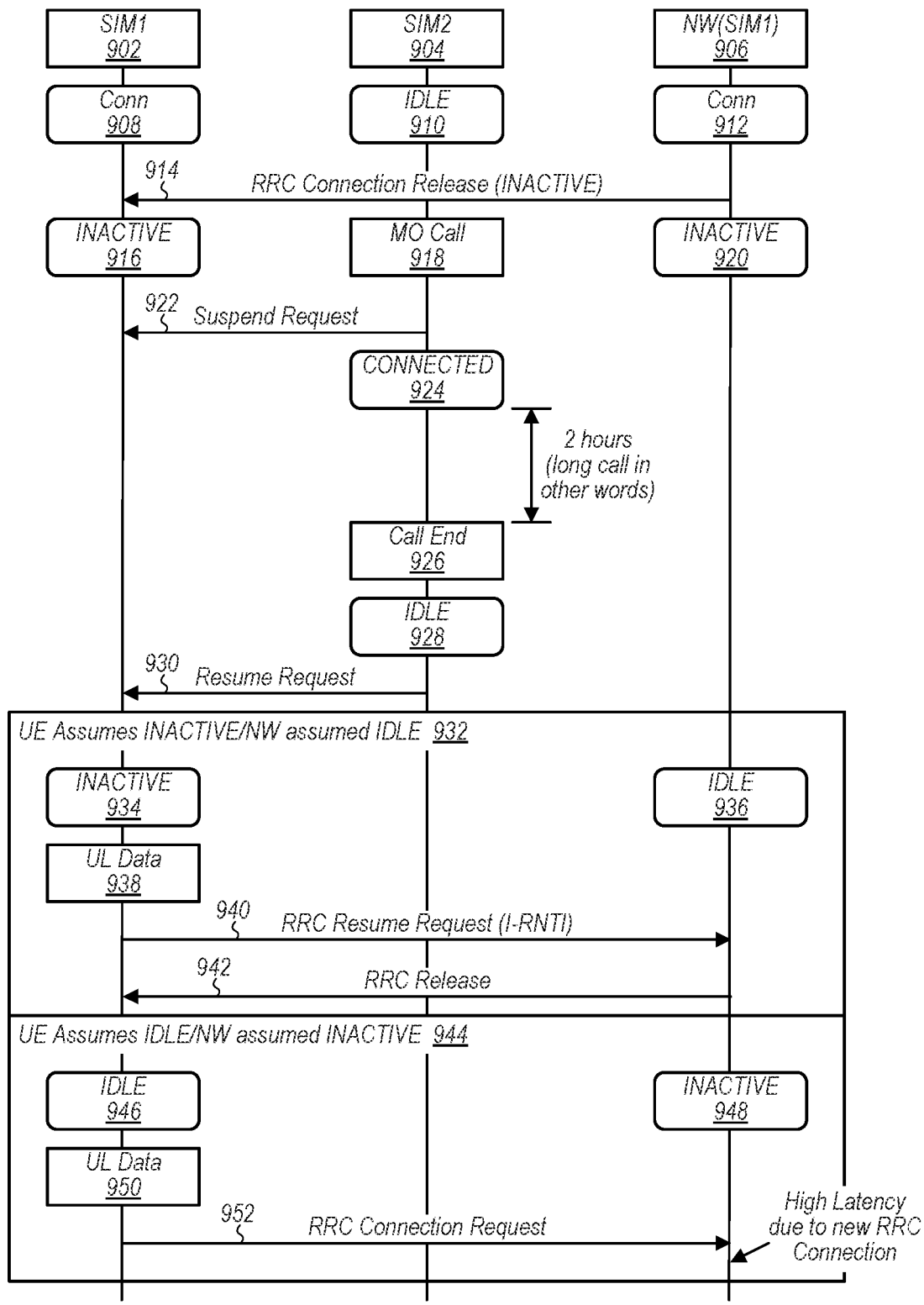
FIG. 9 is a message sequence chart illustrating problems that arise due to RRC state mismatch.

FIG. 9 is a message sequence chart which illustrates issues that may arise in some existing implementations of a DSDS device. Similar to FIGS. 6-8, the message sequence chart of FIG. 9 illustrates the various messaging between a first communication software stack operating with a first SIM (SIM1 902), a second communication software stack operating with a second SIM (SIM2 904), and the cellular network (NW (SIM1) 906) communicating with the first SIM. However, FIG. 9 may be more particularly applicable to 5G NR implementations which utilize an RRC Inactive state. The first communication software stack operating with SIM1 may be in Connected mode 908 performing data transfers with NW (SIM1) using the radio (RF) of the UE 106. As shown, the Network NW (SIM1) is also in Connected mode 912 since it is communicating with the first communication software stack. Since the UE contains only a single radio, when the radio is being used by SIM1 (used by the first communication software stack operating with SIM1), then SIM2 (the second communication software stack operating with SIM2) is in Idle mode 910. In the following discussion, the term "SIM1" is used to refer to the first communication software stack operating in conjunction with SIM1, and similarly "SIM2" is used to refer to the second communication software stack operating in conjunction with SIM2.

At 914, the NW (SIM1) may transmit an RRC connection release message to SIM1, to transition the connection between SIM1 and NW (SIM1) from Connected mode to Inactive mode. SIM1 and NW (SIM1) may then both transition their mutual connection to the Inactive mode.

At 918, a voice call is initiated (or received) by SIM2. As shown in this example, a mobile originating (MO) call is made or placed by the user of the UE, where the MO call is performed using SIM2, which may be a high priority call. In response to the MO call being initiated, SIM2 transmits a Suspend Request 922 to SIM1 to indicate that SIM2 would like to take over the RF chain of the UE to implement the MO call.

At 924, SIM2 may enter an RRC Connected state with its cellular network (e.g., NW (SIM2), not shown in FIG. 9), and may conduct the MO call with a remote entity over NW (SIM2). The MO call may be conducted for a long period of time (e.g., several hours or another long period of time) before the call is ended at 926 and the connection between SIM2 and NW (SIM2) transitions to the Idle state at 928.

After SIM1 receives the resume request from SIM2 at 930, one of two alternative procedures may occur which are illustrated in the two large boxes corresponding to steps 932-942 and steps 944-952, respectively. In the first alternative, when SIM1 receives the resume request from SIM2 at 930, the UE may assume that it is in an Inactive state 934 with NW (SIM1), while NW (SIM1) assumes that the UE is in an Idle state 936. In other words, there may be a mismatch between the UEs and NW (SIM1)'s understanding of the state of the connection between SIM1 and NW (SIM1). As one example, the MO call over SIM2 may have lasted long enough such that NW (SIM1) has abandoned the context associated with its connection with SIM1 and transitioned the connection to Idle state, while the UE thinks that the connection is in the Inactive state. For example, the NW (SIM1) may have attempted to page SIM1 during the SIM2 call, and may have timed out the connection with SIM1 because it did not receive a timely response from SIM1. In these embodiments, SIM1 may have UL data to transmit at 938 and may transmit an RRC resume request with an inactive radio network temporary identifier (I-RNTI) indicator to NW (SIM1) at 940 to resume transmission of the UL data. However, because NW (SIM1) no longer holds the context of the connection, NW (SIM1) may respond with an RRC release message at 942 to release the RRC connection, increasing latency of the UL transmission.

In the second alternative illustrated in reference to steps 944-952, an alternative mismatch may exist between the assumptions of the connection status by SIM1 and NW (SIM1). For example, the UE may assume the connection between SIM1 and NW (SIM1) has been terminated and is in an Idle state at 946, while NW (SIM1) may maintain the connection context in an Inactive mode at 948. In these embodiments, if SIM1 has UL data to transmit to NW (SIM1) at 950, it may transmit an RRC Connection Request to NW (SIM1) at 952 to establish a new connection, thus causing high latency during the setup of a new RRC connection. Embodiments described below present methods and devices to reduce the latency and battery drain introduced in both of these alternatives.

Utilization of Suspension Timer to Avoid RRC State Mismatch

Figure 10:
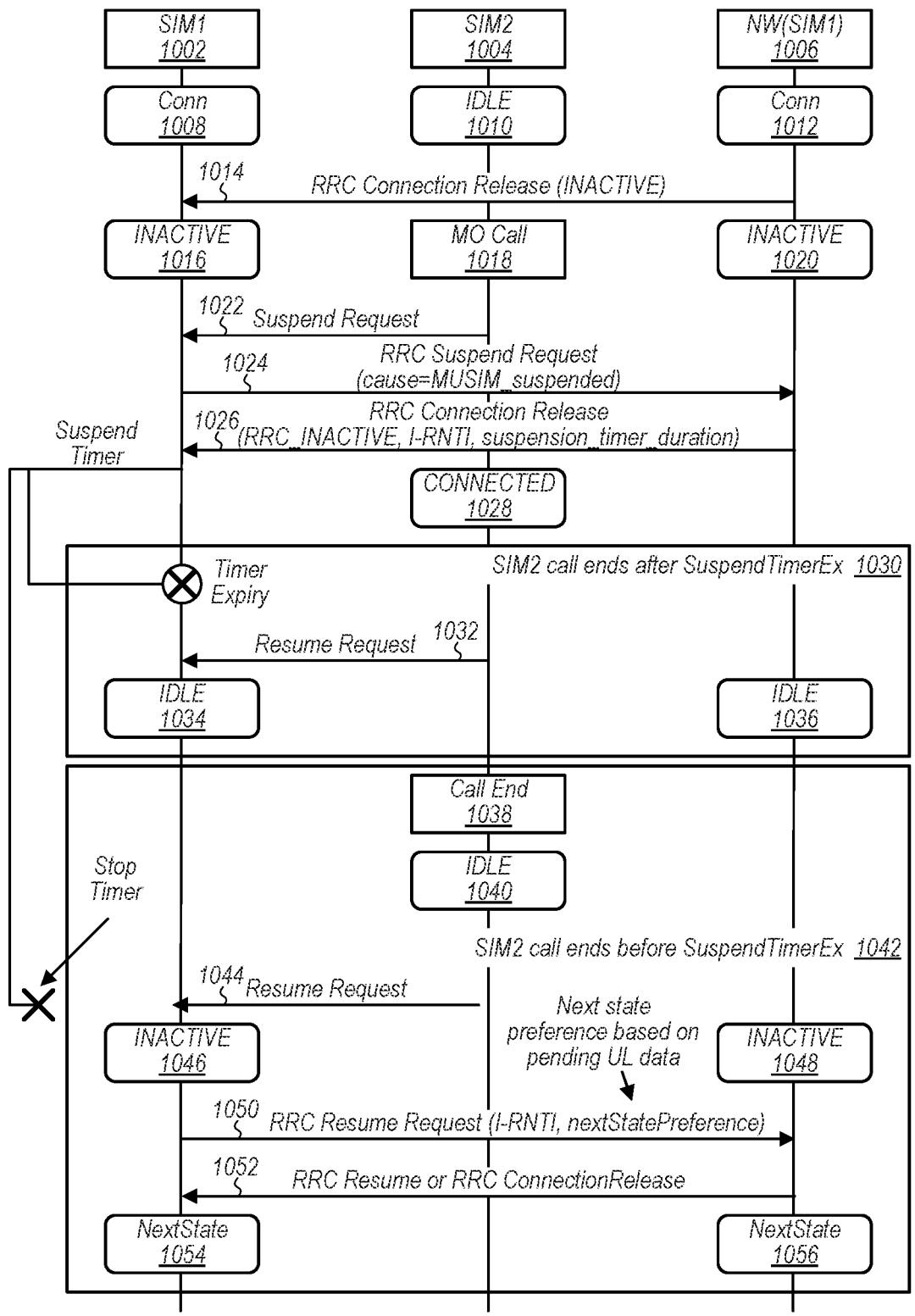
FIG. 10 is a message sequence chart illustrating an example method where a suspension timer is utilized to avoid RRC state mismatch, according to some embodiments.

FIG. 10 is a message sequence chart which illustrates methods and devices that utilize a suspension timer to enhance operation of a DSDS device, according to some embodiments. More specifically, FIG. 10 is a message sequence chart that address some of the limitations and latencies introduced in the message sequence chart illustrated in FIG. 9. Similar to FIGS. 6-9, the message sequence chart of FIG. 10 illustrates the various messaging between a first communication software stack operating with a first SIM (SIM1 1002), a second communication software stack operating with a second SIM (SIM2 1004), and the cellular network (NW (SIM1) 1006) communicating with the first SIM. However, FIG. 10 may be more particularly applicable to 5G NR implementations which utilize an RRC Inactive state. The first communication software stack operating with SIM1 may be in Connected mode 1008 performing data transfers with NW (SIM1) using the radio (RF) of the UE 106. As shown, the Network NW (SIM1) is also in Connected mode 1012 since it is communicating with the first communication software stack. Since the UE contains only a single radio, when the radio is being used by SIM1 (used by the first communication software stack operating with SIM1), then SIM2 (the second communication software stack operating with SIM2) is in Idle mode 1010. In the following discussion, the term "SIM1" is used to refer to the first communication software stack operating in conjunction with SIM1, and similarly "SIM2" is used to refer to the second communication software stack operating in conjunction with SIM2.

Steps 1008-1022 of FIG. 10 may operate similarly to steps 908-922 of FIG. 9, whereby a connection between SIM1 and NW (SIM1) transitions from a Connected state to an Inactive state. Alternatively, in some embodiments, the network may not support the Inactive state and may transition the connection SIM1 and NW (SIM1) to an Idle state (not shown in FIG. 10). Subsequently, SIM2 transitions its connection with NW (SIM2) away from an Idle state to initiate a MO call, and SIM2 transmits a suspend request to SIM1 to obtain access to the shared RF chain of the UE. However, subsequent steps of FIG. 10 diverge from that illustrated in FIG. 9.

In particular, at 1024, SIM1 may transmit an RRC suspend request to NW (SIM1) with a MUSIM_suspended cause indication, to indicate to NW (SIM1) that SIM1 is entering a suspended Inactive state. At 1026, NW (SIM1) may respond by transmitting an RRC connection release message to SIM1 with an RRC_Inactive indication, an I-RNTI, and/or an indication of a suspension timer duration. The UE and NW (SIM1) may both initiate a suspension timer responsive to the transmission of the RRC connection release at step 1026, and SIM2 may establish a Connected state with NW (SIM2) at 1028 to conduct the MO call.

Subsequently, one of two alternative procedures may be implemented, depending on whether the MO call over SIM2 has ended by the time the suspend timer has expired, as described in the two large boxes of FIG. 10 related to steps 1030-1036 and 1038-1056, respectively.

In the first alternative, the suspend timer may expire and the SIM2 call may end subsequent to expiry of the suspend timer at 1030. AT 1032, SIM2 may transmit a resume request to SIM1. However, because the suspend timer has expired, the UE may realize that the connection between SIM1 and NW (SIM1) has been terminated, and both the UE and NW (SIM1) may consider their connection to be in an Idle state. Accordingly, to resume communication over SIM1 with NW (SIM1), SIM1 may initiate a new RRC connection with NW (SIM1) without a mismatch in connection status between the UE and NW (SIM1).

In the second alternative, the SIM2 call may end at 1038 and the connection between SIM2 and NW (SIM2) may enter an idle state at 1040 prior to expiration of the suspend timer. In these embodiments, SIM2 may transmit a resume request to SIM1 at 1044, and SIM1 may assume that the connection between SIM1 and NW (SIM1) remains in the Inactive state at 1046. Accordingly, at 1050, SIM1 may transmit an RRC resume request to NW (SIM1), including an I-RNTI and a nextStatePreference indicator. The nextStatePreference indicator may indicate a preferred state of the UE for the connection between SIM1 and NW (SIM1). For example, if the UE has remaining UL data that it would like to transmit over SIM1, it may request to transition the SIM1/NW (SIM1) connection to a Connected state to transmit the UL data. Alternatively, if the UE has no further data to transmit over SIM1, the nextStatePreference indicator may indicate a preference for either an Inactive or an Idle state, according to various embodiments. Because NW (SIM1) also maintains the suspend timer, it maintains the connection context with SIM1 in an Inactive state when it receives the RRC resume request from SIM1. Accordingly, NW (SIM1) may respond to SIM1 with either an RRC Resume or an RRC ConnectionRelease message, depending on the nextStatePreference indicator and/or network-side considerations. At 1054 and 1056, SIM1 and NW (SIM1) may proceed to operate according to the next state (e.g., either Connected mode, Inactive mode, or Idle mode).

Network Coordination to Avoid RRC State Mismatch

Figure 11:
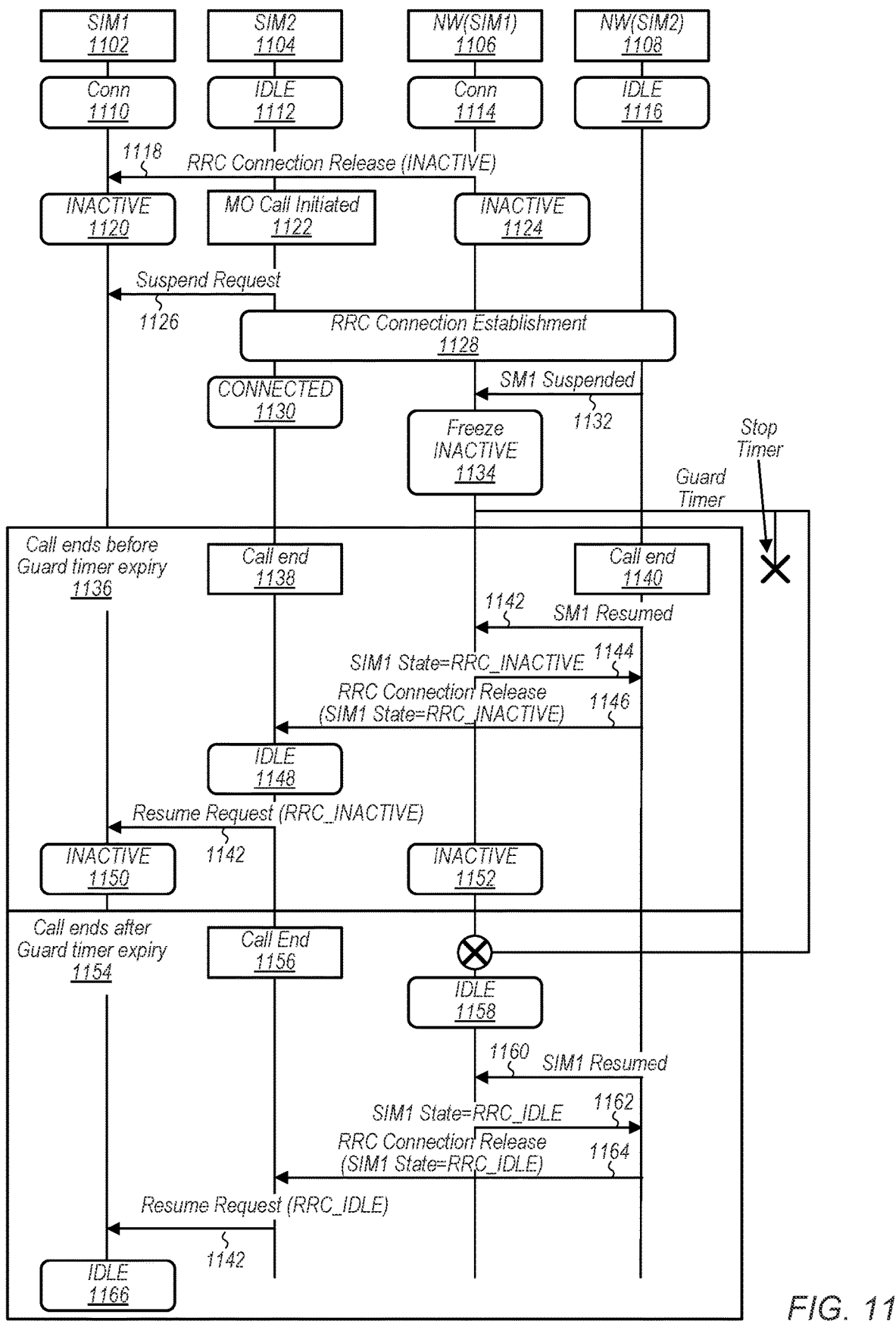
FIG. 11 is a message sequence chart illustrating an example method where network coordination is utilized to avoid RRC state mismatch, according to some embodiments.

FIG. 11 is a message sequence chart which illustrates methods and devices that utilize network-side coordination to enhance operation of a DSDS device, according to some embodiments. More specifically, FIG. 11 is a message sequence chart that utilizes network-side coordination to improve RRC connection state matching between a network and a UE for a DSDS device. Similar to FIGS. 6-10, the message sequence chart of FIG. 11 illustrates the various messaging between a first communication software stack operating with a first SIM (SIM1 1102), a second communication software stack operating with a second SIM (SIM2 1104), a first cellular network (NW (SIM1) 1106) communicating with the first SIM, and a second cellular network (NW (SIM2) 1108) communicating with the second SIM. FIG. 11 may be more particularly applicable to 5G NR implementations which utilize an RRC Inactive state. The first communication software stack operating with SIM1 may be in Connected mode 1110 performing data transfers with NW (SIM1) using the radio (RF) of the UE 106. As shown, the Network NW (SIM1) is also in Connected mode 1114 since it is communicating with the first communication software stack. Since the UE contains only a single radio, when the radio is being used by SIM1 (used by the first communication software stack operating with SIM1), then SIM2 (the second communication software stack operating with SIM2) is in Idle mode 1112, and NW (SIM2) may likewise be in Idle mode 1116 in regard to its connection with SIM2. In the following discussion, the term "SIM1" is used to refer to the first communication software stack operating in conjunction with SIM1, and similarly "SIM2" is used to refer to the second communication software stack operating in conjunction with SIM2.

Steps 1110-1126 of FIG. 11 may operate similarly to steps 908-922 of FIG. 9 and steps 1008-1022 of FIG. 10, whereby a connection between SIM1 and NW (SIM1) transitions from a Connected state to an Inactive state. Alternatively, in some embodiments, the network may not support the Inactive state and may transition the connection between SIM1 and NW (SIM1) to an Idle state (not shown in FIG. 11). Subsequently, SIM2 transitions its connection with NW (SIM2) away from an Idle state to initiate a MO call, and SIM2 transmits a suspend request to SIM1 to obtain access to the shared RF chain of the UE. However, subsequent steps of FIG. 11 diverge from that illustrated in FIGS. 9 and 10.

In particular, at 1128, SIM2 may initiate an RRC Connection Establishment procedure with NW (SIM2) and enter an RRC Connected state at 1130. At 1132, NW (SIM2) may notify NW (SIM1) that the Inactive mode connection between SIM1 and NW (SIM1) should enter a suspended Inactive state. In response, at 1134, NW (SIM1) may freeze its Inactive mode connection with SIM1 and initiate a guard timer.

Subsequently, one of two alternative procedures may be implemented, depending on whether the MO call over SIM2 has ended by the time the guard timer has expired, as described in the two large boxes of FIG. 11 related to steps 1136-1152 and 1154-1166, respectively.

In the first alternative, the SIM2 call may end at 1138 and 1140, prior to expiration of the suspend timer. At 1142, NW (SIM2) may send a Resume indication to NW (SIM1), indicating that NW (SIM1) may resume its connection with SIM1. In response, at 1144 NW (SIM1) may transmit an SIM1 state indicator to NW (SIM2) indicating a preferred RRC state with which to resume its connection for SIM1. For example, in FIG. 11 the SIM1 state indicator indicates a preference for the RRC Inactive state, but NW (SIM1) may also indicate a preference for an RRC Connected state or an RRC Idle state, as desired.

At 1146, NW (SIM2) may transmit an RRC Connection Release message to SIM2 to release the connection between NW (SIM2) and SIM2 so that SIM2 may enter Idle mode. Importantly, NW (SIM2) may include the SIM1 preferred state indicator in the RRC Connection Release message, thereby informing SIM2 of the preferred RRC state for the connection between SIM1 and NW (SIM1). Advantageously, this may preserve state coordination between SIM1 and NW (SIM1) without expending additional radio resources by sending coordination messages between SIM1 and NW (SIM1).

At 1148, SIM2 may send a resume request to SIM1 indicating that SIM2 is relinquishing access to the RF chain of the UE to SIM1, and may include the SIM1 preferred state indicator in the resume request (e.g., SIM2 indicates to SIM1 that NW (SIM1) would like to resume its connection with SIM1 in the Inactive mode in FIG. 11, although the SIM1 preferred state indicator may also indicate a preference for either the Connected mode or the Idle mode, as desired). Finally, at 1150 and 1152, both SIM1 and NW (SIM1) may resume their connection without a suspension according to the preferred state indicator. Accordingly, to communication over SIM1 with NW (SIM1) may be resumed without a mismatch in connection status between the UE and NW (SIM1).

In the second alternative described in reference to steps 1154-1166, the guard timer may first expire and the SIM2 call may end at 1156 subsequent to expiry of the suspend timer. At 1158, NW (SIM1) may transition its connection with SIM1 from the Inactive state to the Idle state responsive to expiry of the guard timer. At 1160, subsequent to the call between SIM2 and NW (SIM2) ending at 1156, NW (SIM2) may send a SIM1 Resume indicator to NW (SIM1), indicating that NW (SIM2) has ended its MO call with SIM2 such that NW (SIM1) may resume its connection with SIM1. However, since NW (SIM1) has already entered the Idle mode with respect to its connection with SIM1 and no longer holds the context for the connection, NW (SIM1) responds to NW (SIM2) with a preferred SIM1 state indicator indicating a preference for the RRC Idle state. Similar to step 1146 described above, at 1164 NW (SIM) send an RRC Connection Release message to SIM2 including the SIM1 preferred state indicator indicating a preference for SIM1 to enter the Idle state. Finally, at 1142 SIM2 may send a resume request to SIM1 indicating that SIM2 is relinquishing access to the RF chain of the UE to SIM1, and further including the SIM1 preferred state indicator for the Idle state, whereupon SIM1 enters the Idle state at 1166. Accordingly, SIM1 and NW (SIM1) will both have transitioned to the Idle state, thus avoiding a state mismatch regarding their connection without explicitly sending coordination messages between SIM1 and NW (SIM1).

Figure 12:
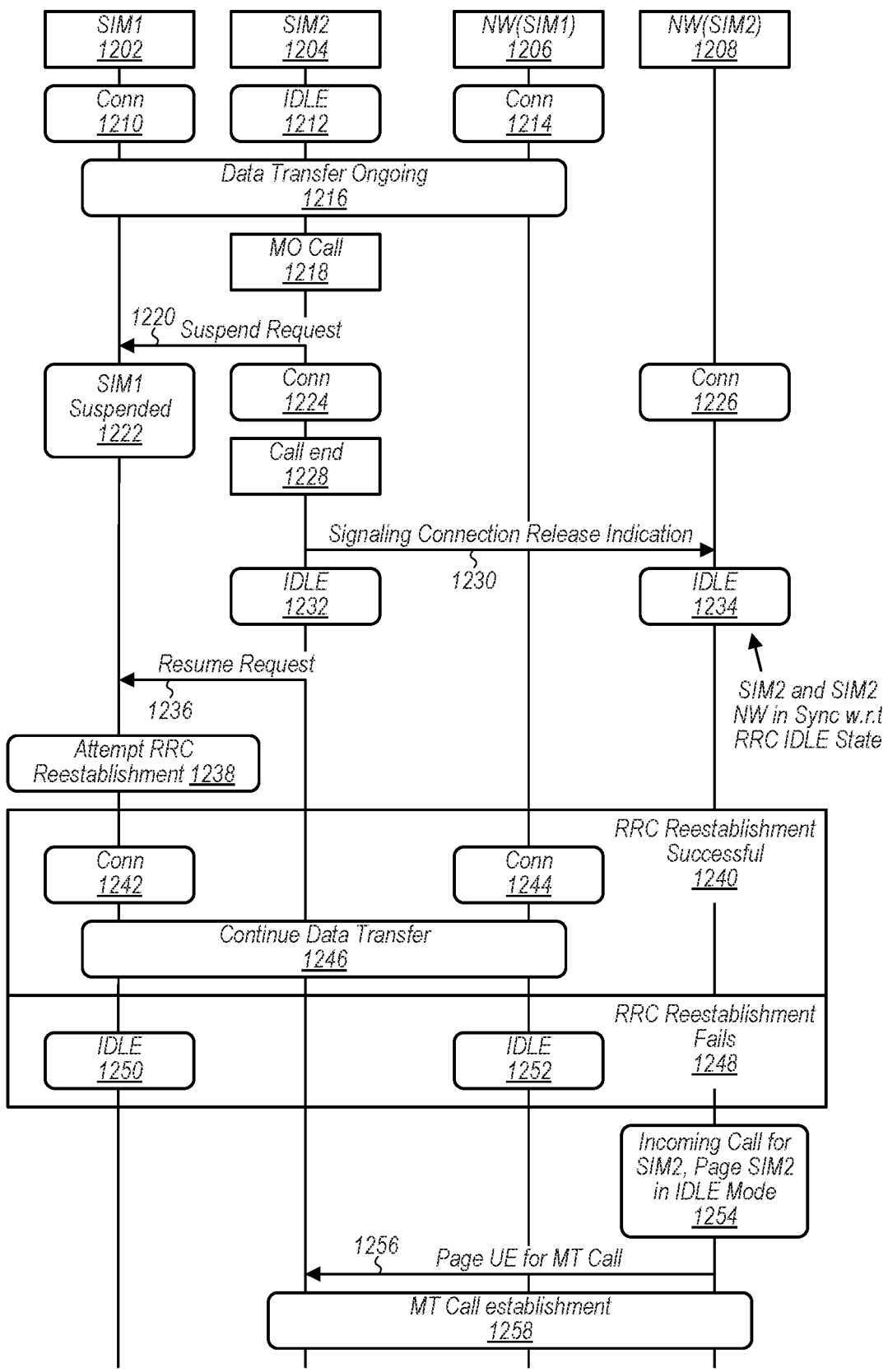
FIG. 12 is a message sequence chart illustrating an example method where a UE informs a network of connection release to avoid RRC state mismatch, according to some embodiments.

FIG. 12—UE Informing Network of Connection Release

FIG. 12 is a message sequence chart which illustrates an alternative embodiment. Similar to FIGS. 6-11, the message sequence chart of FIG. 12 illustrates the various messaging between a first communication software stack operating with a first SIM (SIM1), 1202, a second communication software stack operating with a second SIM (SIM2), 1204, the cellular network (NW (SIM1)) 1206 communicating with the first SIM, and the cellular network (NW (SIM2)) 1208 communicating with the second SIM. The first communication software stack operating with SIM1 may be in Connected mode 1210, 1214, performing ongoing data transfers 1216 with NW (SIM1) using the radio (RF) of the UE 106, while SIM2 is in an Idle state with regard to its connection with NW (SIM2). As shown, the Network NW (SIM1) is also in Connected mode since it is communicating with the first communication software stack of SIM1. Since the UE contains only a single radio, when the radio is being used by SIM1 (used by the first communication software stack operating with SIM1), then SIM2 (the second communication software stack operating with SIM2) is in Idle mode 1210. In the following discussion, the term "SIM1" is used to refer to the first communication software stack operating in conjunction with SIM1, and similarly "SIM2" is used to refer to the second communication software stack operating in conjunction with SIM2.

In some embodiments, when a non-data-preferred SIM (e.g., SIM1) ends a voice call, it will relinquish the RF chain of the UE to the data-preferred SIM (e.g., SIM2) so that SIM2 may continue a data transfer procedure that was suspended due to the SIM1 voice call. In this case, there may be an RRC state mismatch between SIM1 and NW (SIM1) since the UE may typically perform only a local release of the RRC Connection on SIM1 and may cause a mismatch with NW (SIM1). Subsequently, if a MO user triggers back to back voice calls on SIM1, the 2nd call may be missed due to the RRC state mismatch. To address these and other concerns, FIG. 12 presents a method for the UE to inform the NW of a connection release to avoid a potential RRC state mismatch.

While the data transfer 1216 is ongoing between SIM1 and NW (SIM1), a high priority call may be initiated or received by SIM2 at 1218. In response, at 1220, SIM2 may send a suspend request to SIM1 so that SIM2 can obtain access to the radio of the UE. SIM2 may then establish a connection with NW (SIM2) at 1224 and 1226 to conduct the high priority call, and SIM1 may enter a suspended state at 1222.

The high priority call may end at 1228, and SIM2 may send a Signaling Connection Release Indication to NW (SIM2) at 1230 to inform the network that SIM2 is entering the Idle state at 1232. Correspondingly, in response to receiving the Signaling Connection Release Indication from SIM2, NW (SIM2) may also enter an Idle state with respect to its connection SIM2, such that SIM2 and NW (SIM2) are in sync with respect to their mutual connection state.

At 1236, in response to entering the Idle state, SIM2 may send a Resume Request to SIM1 so that SIM1 may resume its connection with NW (SIM1), and SIM1 may attempt to reestablish its RRC Connection with NW (SIM1) at 1238.

At this point, one of two alternative embodiments may be implemented, depending on whether the attempt to reestablish a connection between SIM1 and NW (SIM1) is successful. If reestablishing the connection is successful 1240, the connection may be established at 1242 and 1244, and SIM1 and NW (SIM1) may continue to transfer data in uplink and/or downlink. alternatively, if the attempt to reestablish the connection between SIM1 and NW (SIM1) is unsuccessful at 1248, both SIM1 and NW (SIM1) may enter the Idle state with regard to their mutual connection.

At 1254, NW (SIM2) may be notified of an incoming call for SIM2 at 1254, and NW (SIM2) may page SIM2 in Idle mode for the mobile-terminated (MT) call at 1256. Accordingly, SIM2 may establish the MT call at 1258.

The following paragraphs describe additional embodiments of the invention.

A cellular network device may comprise a processing element; and a memory coupled to the processing element; wherein the cellular network device is configured to: establish a first radio resource control (RRC) connection with a first software communication stack of a user equipment (UE), wherein the first software communication stack uses a first subscriber identity module (SIM) of the UE; receive a radio resource control (RRC) connection suspend request from the first software communication stack of the UE, wherein the RRC connection suspend request comprises information specifying a cause of the suspend request as being a higher priority cellular communication of a second software communication stack using a second SIM of the UE; and store a connection state of the RRC connection of the first software communication stack of the UE, wherein the stored connection state is usable to restore the RRC connection at a later time.

In some embodiments, the cellular network device may be further configured to: receive an RRC resume request from the first software communication stack of the UE, wherein the RRC resume request is received a period of time after receiving the RRC connection suspend request; and restore the stored connection state of the RRC connection with the first software communication stack of the UE.

In some embodiments, the cellular network device may be further configured to discontinue transfer of downlink data to the UE in response to receiving the RRC connection suspend request.

In other embodiments, a cellular network entity may comprise a radio, comprising one or more antennas for performing wireless communication; and a processing element operatively coupled to the radio; wherein the cellular network entity is configured to: establish a first radio resource control (RRC) connection with a first subscriber identity module (SIM) of a user equipment device (UE), wherein the first RRC connection is in an inactive mode; receive a first notification from a second cellular network entity to suspend the first RRC connection; in response to receiving the first notification, suspend the first RRC connection and initiate a guard timer; receive a second indication from the second cellular network entity to resume the first RRC connection; transmit a preferred state indicator to the second cellular network entity indicating a preferred state for resuming the first RRC connection; and resume the first RRC connection with the first SIM of the UE according to the preferred state.

In some embodiments, the cellular network may operate such that the second indication is received after expiration of the timer, and the preferred state indicator indicates a preference for an RRC idle state.

In some embodiments, the cellular network may operate such that the second indication is received before expiration of the timer, and the preferred state indicator indicates a preference for either an RRC inactive state or an RRC connected state.

In some embodiments, a wireless user equipment (UE) device comprises a radio, comprising one or more antennas for performing wireless communication, a processing element operatively coupled to the radio, and first and second subscriber identity modules (SIMs). Each of the first and second SIMs is coupled to the radio and configured to be used with the radio for wireless communication, wherein only one of the first and second SIMs is used with the radio at any given time. The UE may be configured to perform cellular data communications with a first cellular network using the first SIM and a first radio resource control (RRC) connection; and receive a request to perform a higher priority cellular communication with a second cellular network using the second SIM. In response to the request to perform the higher priority cellular communication using the second SIM, the UE may suspend the first RRC connection and may conduct the higher priority cellular communication with the second cellular network using the second SIM. When the higher priority cellular communication is completed, the UE may send a release indication to the second network, and the UE may resume the first RRC connection with the first SIM.

It is well understood that the use of personally identifiable information should follow privacy policies and practices that are generally recognized as meeting or exceeding industry or governmental requirements for maintaining the privacy of users. In particular, personally identifiable information data should be managed and handled so as to minimize risks of unintentional or unauthorized access or use, and the nature of authorized use should be clearly indicated to users.

Embodiments of the present disclosure may be realized in any of various forms. For example, some embodiments may be realized as a computer-implemented method, a computer-readable memory medium, or a computer system. Other embodiments may be realized using one or more custom-designed hardware devices such as ASICs. Still other embodiments may be realized using one or more programmable hardware elements such as FPGAs.

In some embodiments, a non-transitory computer-readable memory medium may be configured so that it stores program instructions and/or data, where the program instructions, if executed by a computer system, cause the computer system to perform a method, e.g., any of a method embodiments described herein, or, any combination of the method embodiments described herein, or, any subset of any of the method embodiments described herein, or, any combination of such subsets.

In some embodiments, a computer system may be configured to include a processor (or a set of processors) and a memory medium, where the memory medium stores program instructions, where the processor is configured to read and execute the program instructions from the memory medium, where the program instructions are executable to implement any of the various method embodiments described herein (or, any combination of the method embodiments described herein, or, any subset of any of the method embodiments described herein, or, any combination of such subsets). The computer system may be realized in any of various forms. For example, the computer system may be a personal computer (in any of its various realizations), a workstation, a computer on a card, an application-specific computer in a box, a server computer, a client computer, a hand-held device, a user equipment (UE), a tablet computer, a wearable computer, etc.

Although the embodiments above have been described in considerable detail, numerous variations and modifications will become apparent to those skilled in the art once the above disclosure is fully appreciated. It is intended that the following claims be interpreted to embrace all such variations and modifications.

We claim:

1. An apparatus, comprising:
a processor configured to cause a user equipment device (UE) to:
perform cellular data communications with a first cellular network using a first subscriber identity module (SIM) of the UE and a first radio resource control (RRC) connection in a first RRC State associated with the first SIM;
determine that communication activity prompts use of a second SIM of the UE, wherein determining that communication activity prompts use of the second SIM comprises determining a paging message is received in the UE;
in response to determination that the communication activity prompts use of the second SIM, transmit a message to the first cellular network while cellular data communications are being performed with the first RRC connection using the first SIM that requests release of the first RRC connection; and
subsequent to transmitting the message to the first cellular network, release the first RRC connection and change RRC State associated with the first SIM from the first RRC State to a second RRC State.

2. The apparatus of claim 1,
wherein one or more of the first and second SIMs is an embedded SIM using embedded memory in the UE to store subscriber information related to the one or more of the first and second SIM.

3. The apparatus of claim 1,
wherein the use of the second SIM comprises a higher priority use than the cellular data communications.

4. The apparatus of claim 3,
wherein the paging message is received from a second cellular network for the second SIM.

5. The apparatus of claim 1,
wherein the first RRC State is an RRC_Connected State.

6. The apparatus of claim 1,
wherein the UE is further configured to:
transition an RRC State associated with the second SIM from a third RRC State to a fourth RRC State,
wherein the third RRC State is one of an RRC_Idle State or an RRC_Inactive State, and
wherein the fourth RRC State is an RRC_Connected State.

7. The apparatus of claim 1,
wherein the second RRC State is one of an RRC_Idle State or an RRC Inactive State.

8. A method, comprising, by a user equipment device (UE):
performing cellular data communications with a first cellular network using a first subscriber identity module (SIM) of the UE and a first radio resource control (RRC) connection in a first RRC State associated with the first SIM;
determining that communication activity prompts use of a second SIM of the UE, wherein determining that communication activity prompts use of the second SIM comprises determining a paging message is received in the UE;
in response to determination that the communication activity prompts use of the second SIM, transmitting a message to the first cellular network while the cellular data communications are being performed with the first RRC connection using the first SIM, the message requesting release of the first RRC connection; and
subsequent to transmitting the message to the first cellular network, releasing the first RRC connection and changing RRC State associated with the first SIM from the first RRC State to a second RRC State.

9. The method of claim 8,
wherein one or more of the first and second SIMs is an embedded SIM using embedded memory in the UE to store subscriber information related to the one or more of the first and second SIMs.

10. The method of claim 8,
wherein the use of the second SIM comprises a higher priority use than the cellular data communications.

11. The method of claim 10,
wherein the paging message is received from a second cellular network for the second SIM.

12. The method of claim 8,
wherein the first RRC State is an RRC_Connected State.

13. The method of claim 8,
wherein the second RRC State is one of an RRC_Idle State or an RRC_Inactive State.

14. The method of claim 8, further comprising:
transitioning an RRC State associated with the second SIM from a third RRC State to a fourth RRC State,
wherein the third RRC State is one of an RRC Idle State or an RRC_Inactive State, and
wherein the fourth RRC State is an RRC_Connected State.

15. An apparatus, comprising:
a processor configured to cause an access and mobility management function (AMF) to:
using a first cellular network, manage cellular data communications corresponding to a first radio resource control (RRC) connection with a user equipment device (UE) that is using a first subscriber identity module (SIM) of the UE, wherein the UE is in a first RRC State associated with the first SIM;
receive a message from the UE requesting release of the first RRC connection and requesting suspension of paging for the UE associated with the first cellular network while cellular data communications are being performed with the first RRC connection using the first SIM, wherein the message is received responsive to a determination that communication activity prompts use of a second SIM of the UE, wherein determining that communication activity prompts use of the second SIM comprises determining a paging message is received in the UE; and subsequent to receiving the message from the UE, suspend paging associated with the UE, release the first RRC connection and change RRC State associated with the first SIM from the first RRC State to a second RRC State.

16. The apparatus of claim 15,
wherein the AMF manages cellular data communications with the UE through a g Node B (gNB).

17. The apparatus of claim 15,
wherein the use of the second SIM comprises a higher priority use than the cellular data communications.

18. The apparatus of claim 15,
wherein the first RRC State is an RRC_Connected State.

19. The apparatus of claim 15,
wherein the second RRC State is one of an RRC_Idle State or an RRC Inactive State.

\* \* \* \* \*